United States Patent [19]

Sprecker et al.

[11] 4,285,349
[45] Aug. 25, 1981

[54] USE OF CERTAIN BRIDGED KETONES IN AUGMENTING OR ENHANCING THE ORGANOLEPTIC PROPERTIES OF SMOKING TOBACCO

[75] Inventors: Mark A. Sprecker, Sea Bright; James M. Sanders, Eatontown; William L. Schreiber, Jackson; Hugh Watkins, Lincroft; Joaquin F. Vinals, Red Bank, all of N.J.; Edward J. Shuster, Brooklyn, N.Y.; Thomas J. O'Rourke, Red Bank, N.J.; Myrna L. Hagedorn, Highland Park, N.J.; Philip Klemarczyk, Old Bridge, N.J.

[73] Assignee: International Flavors & Fragrances Inc., New York, N.Y.

[21] Appl. No.: 200,045

[22] Filed: Oct. 23, 1980

Related U.S. Application Data

[62] Division of Ser. No. 95,149, Nov. 16, 1979, Pat. No. 4,250,338.

[51] Int. Cl.³ .................. A24B 3/12; A24B 15/30

[52] U.S. Cl. .................................................. 131/276
[58] Field of Search ..................... 131/17 R, 144, 9

*Primary Examiner*—V. Millin
*Attorney, Agent, or Firm*—Arthur L. Liberman

[57] ABSTRACT

Described in a process for augmenting or enhancing the aroma or taste of a smoking tobacco comprising the step of adding to a smoking tobacco an aroma or taste augmenting or enhancing quantity of at least one tricyclic ketone having the structure:

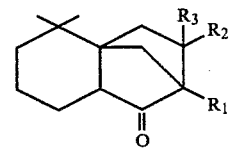

wherein $R_1$, $R_2$ and $R_3$ are the same or different and each represents hydrogen or $C_1$-$C_3$ lower alkyl.

3 Claims, 14 Drawing Figures

FIG.1
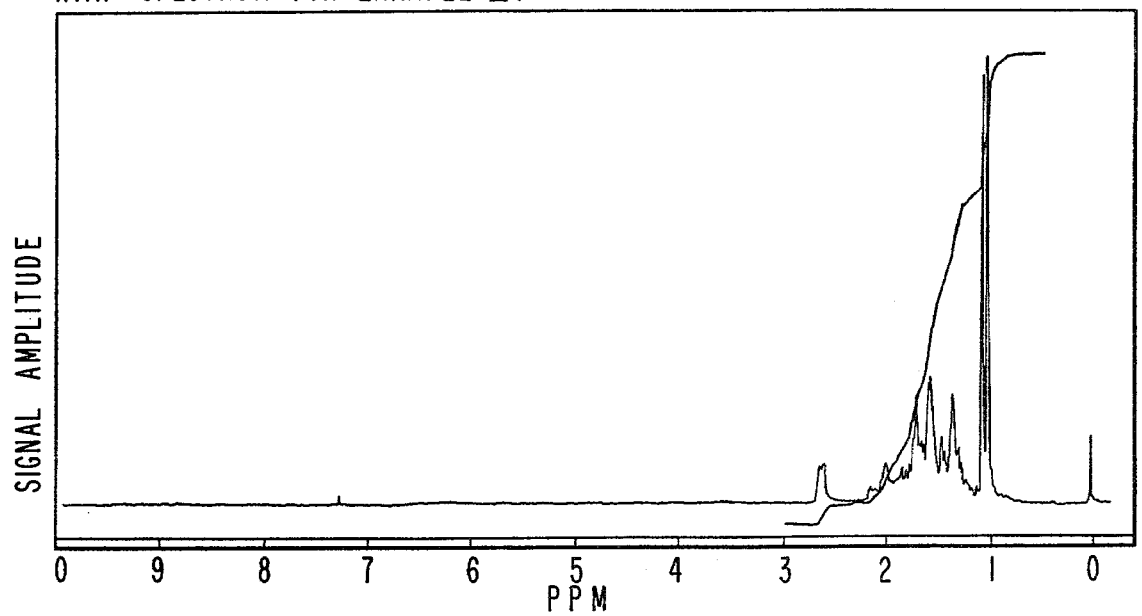
NMR SPECTRUM FOR EXAMPLE I.
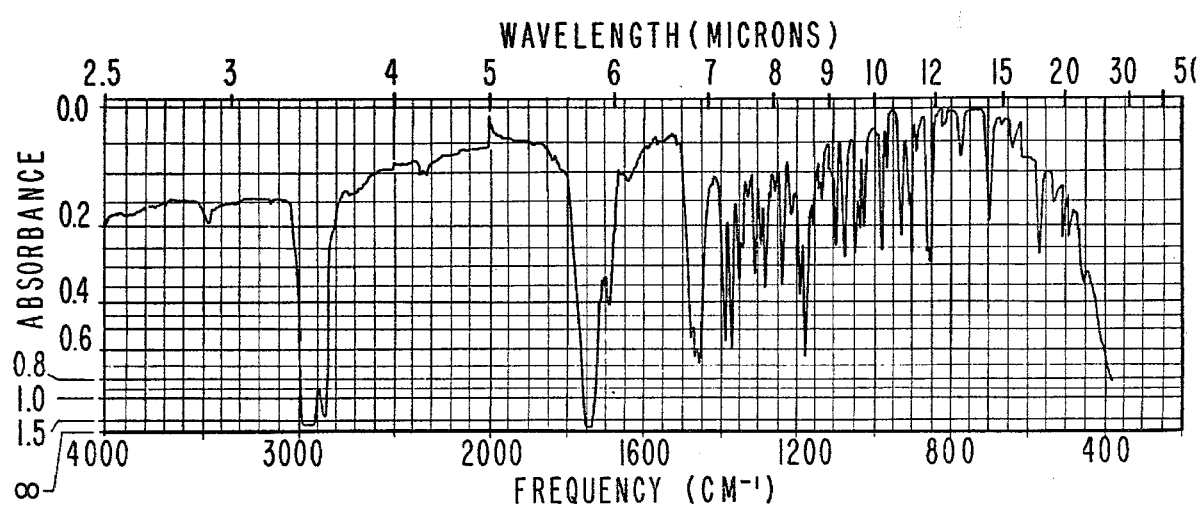
IR SPECTRUM FOR EXAMPLE I.
FIG.2

GLC PROFILE FOR EXAMPLE III.

NMR SPECTRUM FOR EXAMPLE IV.

FIG.5
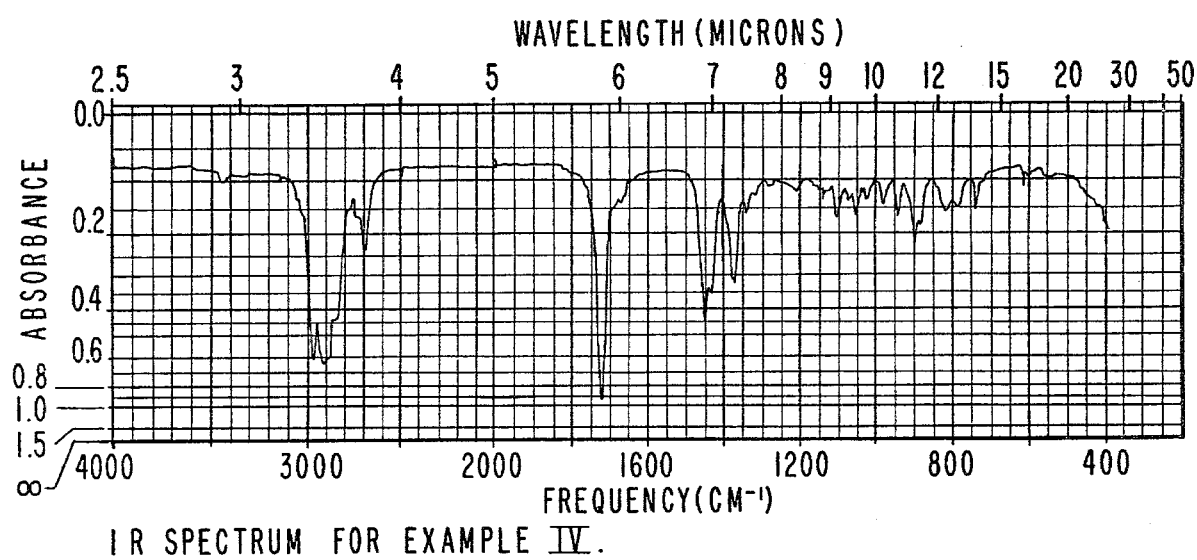
IR SPECTRUM FOR EXAMPLE IV.
NMR SPECTRUM FOR EXAMPLE V.
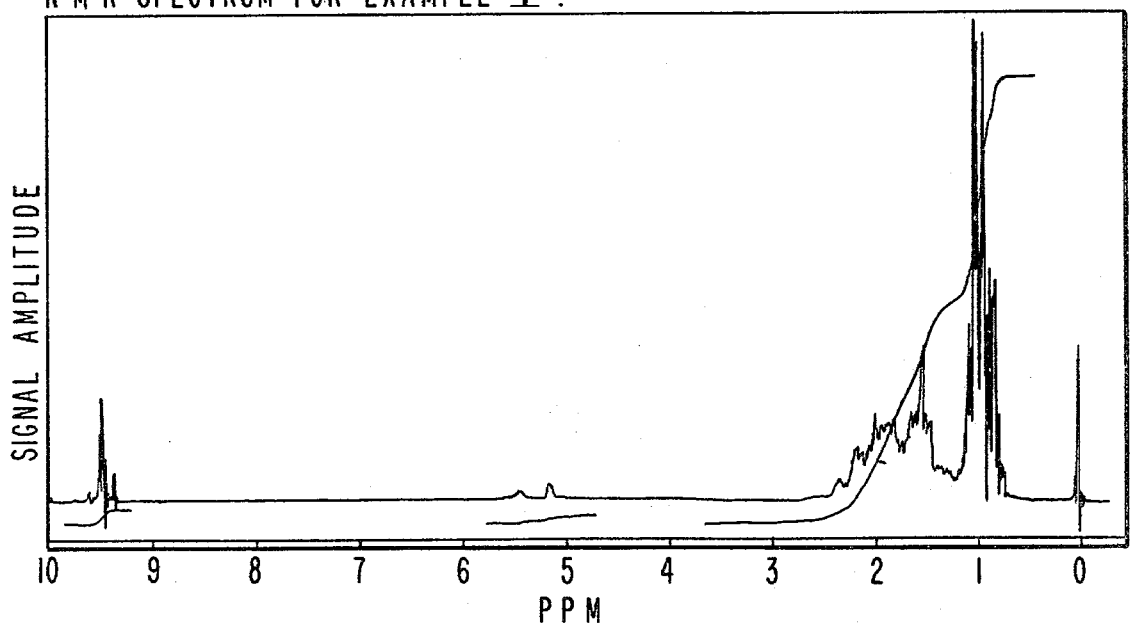
FIG.6

FIG. 7
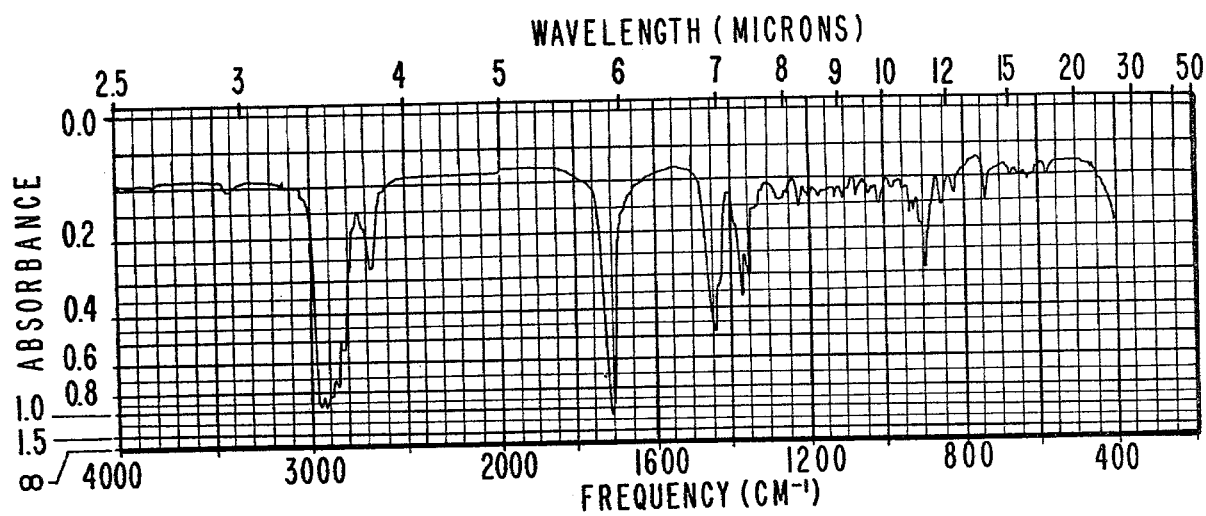
IR SPECTRUM FOR EXAMPLE V.
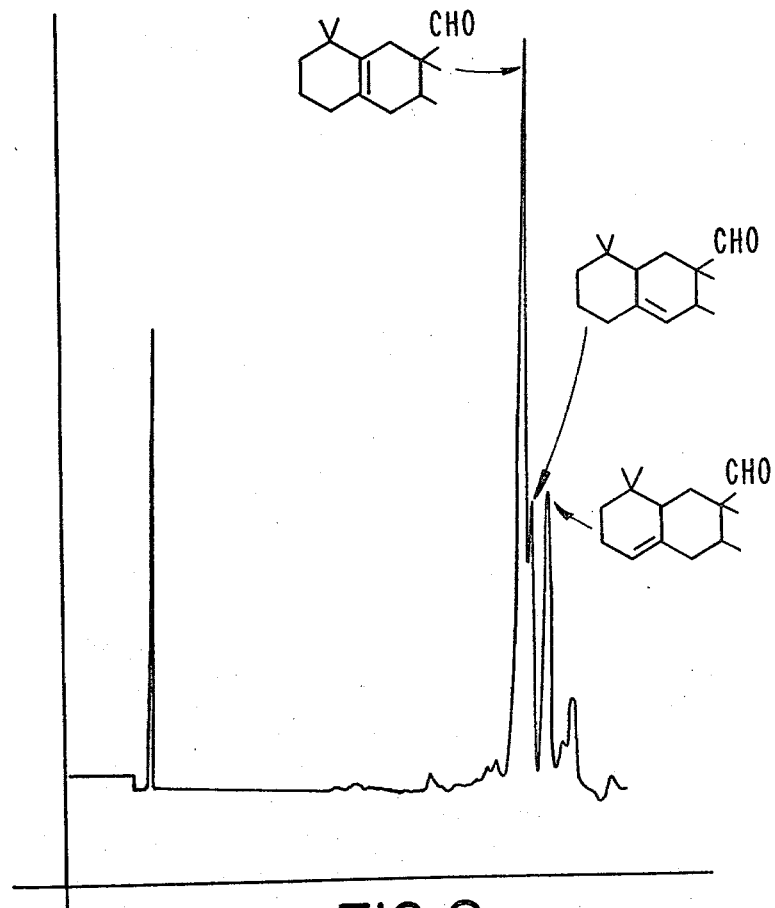
FIG. 8
GLC PROFILE FOR EXAMPLE V.

NMR SPECTRUM FOR EXAMPLE VI.

IR SPECTRUM FOR EXAMPLE VI.

NMR SPECTRUM FOR EXAMPLE VII.

NMR SPECTRUM FOR EXAMPLE VII, FRACTION 16 $^{13}C$

FIG. 13
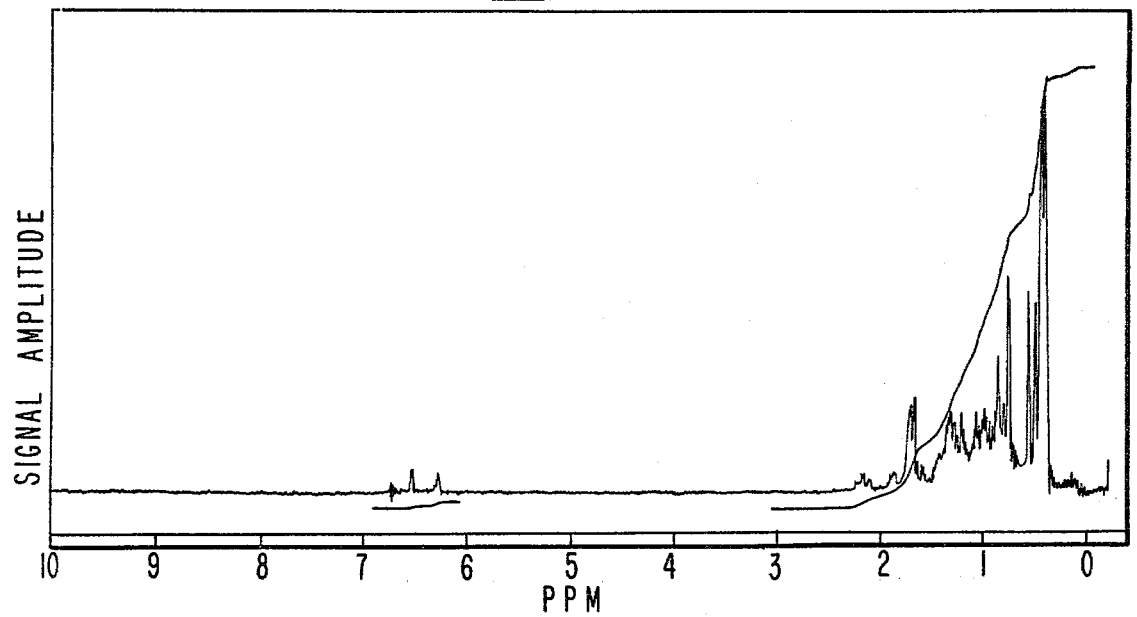
NMR SPECTRUM FOR EXAMPLE VIII.
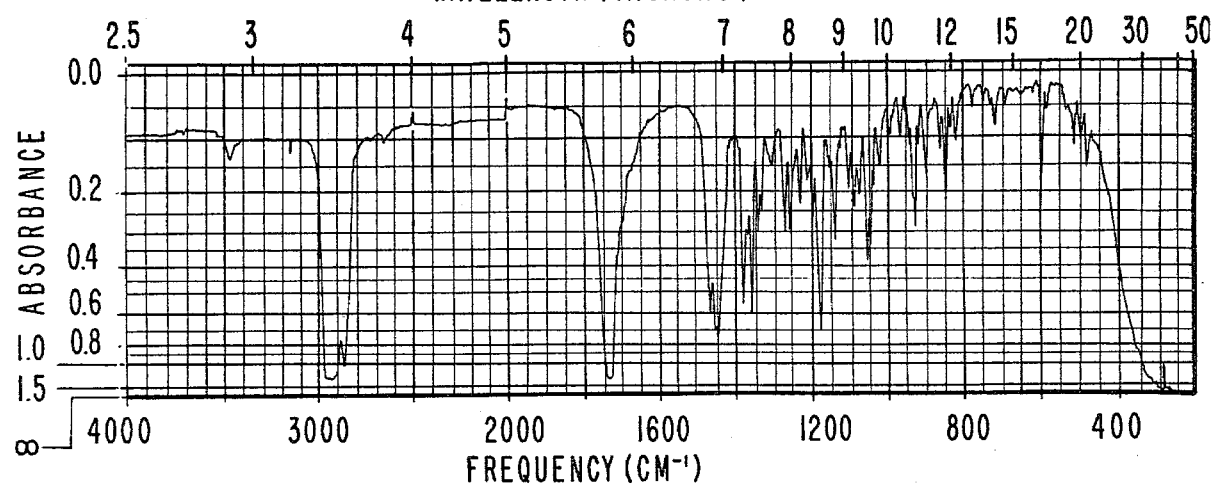
IR SPECTRUM FOR EXAMPLE VIII.
FIG. 14

USE OF CERTAIN BRIDGED KETONES IN AUGMENTING OR ENHANCING THE ORGANOLEPTIC PROPERTIES OF SMOKING TOBACCO

This Application is a Divisional of application for U.S. Patent Ser. No. 95,149 filed on Nov. 16, 1979 now U.S. Pat. No. 4,250,338.

BACKGROUND OF THE INVENTION

This invention relates to compounds having the generic structure:

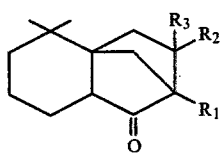

wherein $R_1$, $R_2$ and $R_3$ are the same or different and each represents hydrogen or C1–C3 lower alkyl, processes for preparing same and organoleptic uses thereof in perfumes, colognes, perfumed articles such as anionic, cationic and non-ionic detergents and dryer-added fabric softeners and in smoking tobaccos and smoking tobacco articles which comprise a wrapper encasing a smoking tobacco body and impinging thereupon a smoking tobacco article filter.

There has been considerable work performed relating to substances which can be used to impart (modify, augment or enhance) flavors and fragrances to (or in) various consumable materials. These substances are used to diminish the use of natural materials, some of which may be in short supply, and to provide more uniform properties in the finished product.

Low-keyed, oily, woody amber, leathery, warm spice, earthy, camphoraceous, patchouli-like, balsamic, green, cardamom-like, vetiver-like, sweet woody, amber and minty aromas are desirable in several types of perfume compositions, perfumed articles such an anionic, cationic and non-ionic detergents, cosmetic powders and dryer-added fabric softener articles, and colognes.

Sweet, floral, woody, spicy, leathery and amber aromas prior to smoking and sweet, natural tobacco-like tastes and aromas are desirable in several types of smoking tobaccos, smoking tobacco articles and in smoking tobacco flavoring compositions.

British Pat. No. 896,039 entitled "Method of Producing Derivatives of the 1,1-Dimethyloctahydronaphthalene Series" discloses the generic process.

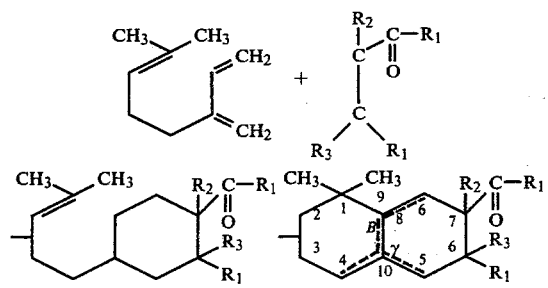

wherein $R_2$, $R_3$ and $R_4$ are disclosed to be same or different hydrogen atoms or alkyl and $R_1$ is disclosed to be hydroxy, alkyl or alkoxy. The British patent discloses this process to be useful for producing products "resembling the well known class of violet perfumes". Indeed, Example 5 of the British patent alleges that the compound 1,1,6,6-Tetramethyl-7-ketomethyl-Octalin produced by (1) reacting myrcene and mesityl oxide thermally followed by (2) subsequent cyclization, has a pleasant "woody ambergris smell". However, a repetition of the teachings of this British patent gives rise to the following results:

STRUCTURE OF COMPOUND

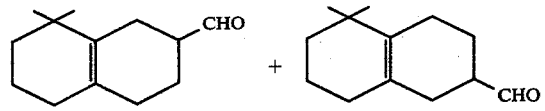

NAME

1', 2', 3', 4', 5', 6',7',8'-octahydro-8', 8'(and 5', 5')dimethyl-2'-naphthaldehyde.

Perfume Properties

Green, fruity

STRUCTURE OF COMPOUND

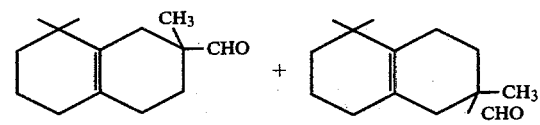

NAME

1', 2', 3', 4', 5', 6', 7', 8'-octahydro-2', 8', 8'(and 2', 5', 5')-trimethyl-2'-napthaldehyde Perfume Properties Green floral, fruity

STRUCTURE OF COMPOUND

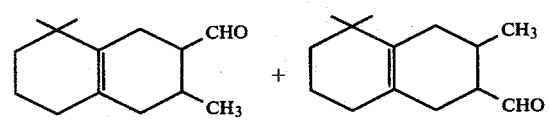

NAME

1', 2', 3', 4', 5', 6', 7', 8'-octahydro-3', 8', 8'(and 3', 5', 5')-trimethyl-2'-naphthaldehyde Perfume Properties Green, buttery, woody U.S. Pat. No. 2,933,506, issued on Apr. 19, 1960, discloses the production of perfume compounds according to the reaction sequence:

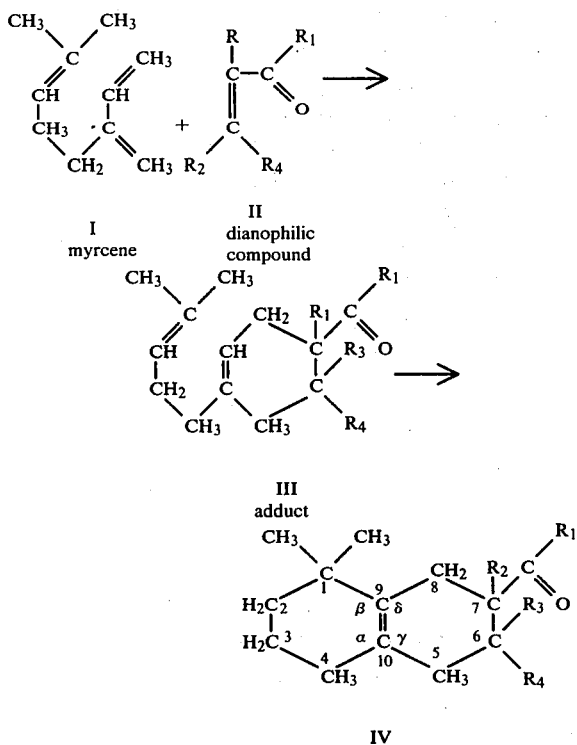

(a) β-isomer of 1,1-dimethyl octaline compound

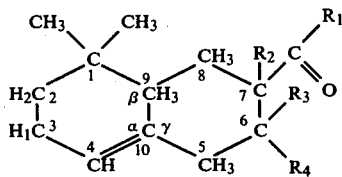

(b) α-isomer of 1,1-dimethyl octaline compound

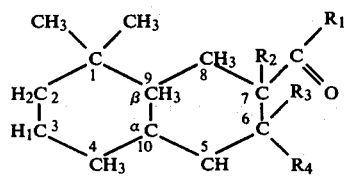

(c) γ-isomer of 1,1-dimethyl octaline compound

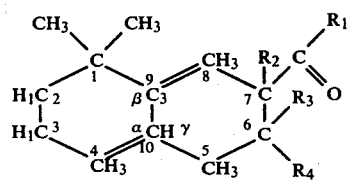

(d) δ-isomer of 1,1-dimethyl octaine compound

In said formula $R_1$, $R_2$, $R_3$, and $R_4$ represent hydrogen or alkyl, especially a lower alkyl radical, aryl, aralkyl, cycloalkyl, or heterocyclic residues. $R_1$ in said formula can also be the hydroxyl group or an ether group. The ether group may form an ester group or a lactone group with the —CO— group.

The new compounds are obtained by first subjecting myrcene of Formula I to the diene synthesis with a dienophilic compound of Formula II. The resulting adduct of Formula III is then subjected to ring closure reaction to form the corresponding 1,1-dimethyl octaline compounds of Formula IV.

Thus, for example, the 1,1-dimethyl-7-methylal octaline can be produced as follows:

576 g. (3 mols) of the aldehyde obtained from myrcene and acrolein, said aldehyde corresponding to Formula III wherein $R_1$, $R_2$, $R_3$, and $R_4$ are hydrogen, are dissolved in 600 cc. of ether. 279 g. (3 mols) of aniline dissolved in 500 cc. of ether are added to said solution portion by portion at room temperature in a separatory funnel while shaking the mixture repeatedly.

After allowing the mixture to stand at room temperature for about 20 hours, the theoretical amount of water has split off. The resulting solution is separated from the water formed on reaction and is directly used for cyclization.

The ethereal solution of the Schiff's base is added drop by drop to 4 of 62% sulfuric acid at −15° C. within about 2 hours while stirring vigorously. Care must be taken that the temperature does not substantially exceed 0° C. After the solution has been added to the sulfuric acid, stirring of the reaction mixture is continued at −5° C. for about one hour. The reaction mixture is then treated with steam until all the solvent has been distilled off. The distillation requires about ½ hour. The reaction mixture has now separated into two layers. It is poured on ice and is exhaustively extracted with benzene. The benzene solution of the bicyclic aldehyde is washed with water until the wash water is substantially neutral. Thereafter, the solvent is distilled off under atmospheric pressure and the residue is subjected to fractional distillation in a vacuum.

In this manner 438 g. of 1,1-dimethyl-7-methylal octaline are obtained. The yield is about 76% of the theoretical yield. The reaction product consists of ½ of the β-compound with the double bond in 9,10-position and to ½ of a substantially uniform isomer, the double bond of which is either in α-, or in γ-, or in δ-position.

Characteristic properties of the mixture of isomers:
Boiling point: 85–86° C./0.5 mm.;
Density $d_4^{20}$: 0.9877;
Index of refraction $n_D^{20}$: 1.5031;
Aldehyde content: 98–100%.

By fractional crystallization of the semicarbonzones of the reaction mixture, the isomers can be separated from each other. For this purpose 70 g. of the bicyclic aldehyde mixture are mixed with a solution of 70 g. of semicarbazide hydrochloride and 70 g. of sodium acetate in 140 cc. of water. Methanol is added until complete solution is achieved. The reaction mixture is allowed to stand overnight at room temperature. 95.5 g. of an amorphous semicarbazone precipitates. It has an upsharp point of decomposition at 139–141° C. On repeated recrystallization from 90% methanol 53.5 g. of white crystals melting at 148° C. with decomposition are obtained.

In order to produce therefrom pure 1,1-dimethyl-7-methylal-Δ9,10-octaline, the semicarbazone was split up by heating with 50 g. of oxalic acid in 200 cc. of water. The aldehyde set free thereby is separated from the reaction solution by vacuum steam distillation. The steam distillate is subjected to fractional distillation in a vacuum. In this manner 30 g. of a very pure aldehyde are obtained. This aldehyde has a pleasant refreshing and sandalwood-like ionone odor.

Characteristic properties of 1,1-dimethyl-7-methylal-$\Delta_{9,10}$-octaline:
Boiling point: 85° C./0.5 mm.;
Density $d_4^{20}$: 0.9914;
Index of refraction $n_D^{20}$: 1.5054;
Aldehyde content: 100%.

After standing for several days at −25° C. there precipitates from the mother liquor of the semicarbazone reaction mixture a second compound which, on repeated recrystallization from methanol, has a melting point of 134° C. 14.5 g. of this semicarbazone are obtained. The aldehyde is set free therefrom by means of oxalic acid in the same manner as described hereinabove for the β-aldehyde.

The position of the double bond in said aldehyde could not yet be ascertained with certainty. The double bond is either in α-, γ-, or δ-position. The compound also has a refreshing ionone aroma, however, without any accompanying sandalwood-like nuance.

Characteristic properties of this isomeric aldehyde:
Boiling point: 85°-86° C./0.5 mm.,
Density $d_4^{20}$: 0.9890;
Index of refraction $n_D^{20}$: 1.5044;
Aldehyde content: 100%.

Another example indicating preparation of 1,1-dimethyl-7-methylal octaline in U.S. Pat. No. 2,933,506 is as follows:

1 mol. of the aldehyde in the form of its Schiff's base as prepared and used in Example 1 is dissolved in an equal amount of benzene. The benzene solution is added drop by drop to 700 cc. of 85% phosphoric acid at 0° C. while stirring vigorously. Thereafter, stirring of the reaction mixture is continued at 60° C. for 1 hour. Thereby not only cyclization is completed but the azomethine group is quantitatively split up. The resulting bicyclic aldehyde is then poured on ice, extracted by means of benzene, and the benzene layer is washed with water until neutral. After distilling off the solvent, 190 g. of residue of an aldehyde content of 82% are obtained. The crude bicyclic aldehyde is subjected to fractional distillation by means of a small fractionating column. In this manner 135 g. of 1,1-dimethyl-7-methylal octaline are obtained. The yield is about 70% of the theoretical yield. The aldehyde consists mainly of an isomer, the double bond of which is either in α-, or in γ-, or in δ-position.

Characteristic properties:

Boiling point: 96° C./0.7 mm.;
Density $d_4^{20}$: 0.9884;
Index of refraction $n_D^{20}$: 1.5042;
Aldehyde content: 98–100%.
Additional reaction of the resulting compounds with acid and heating gives rise to the compounds of our invention having the generic structure:

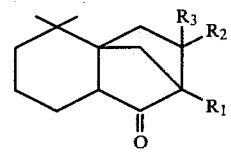

wherein $R_1$, $R_2$ and $R_3$ are the same or different and each represents hydrogen or C1-C3 lower alkyl.

However, there is no inference in any of the pertinent prior art that the tricyclic ketone compounds of our invention can be produced or ever have been produced.

BRIEF DESCRIPTION OF THE DRAWINGS

FIG. 1 represents the NMR spectrum for the tricyclic ketone compound having the structure:

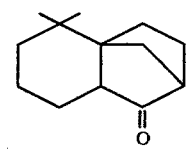

produced according to Example I.

FIG. 2 represents the infra-red spectrum for the tricyclic ketone compound having the structure:

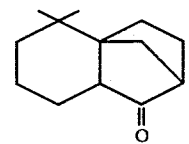

prepared according to Example I.

Figure 3:
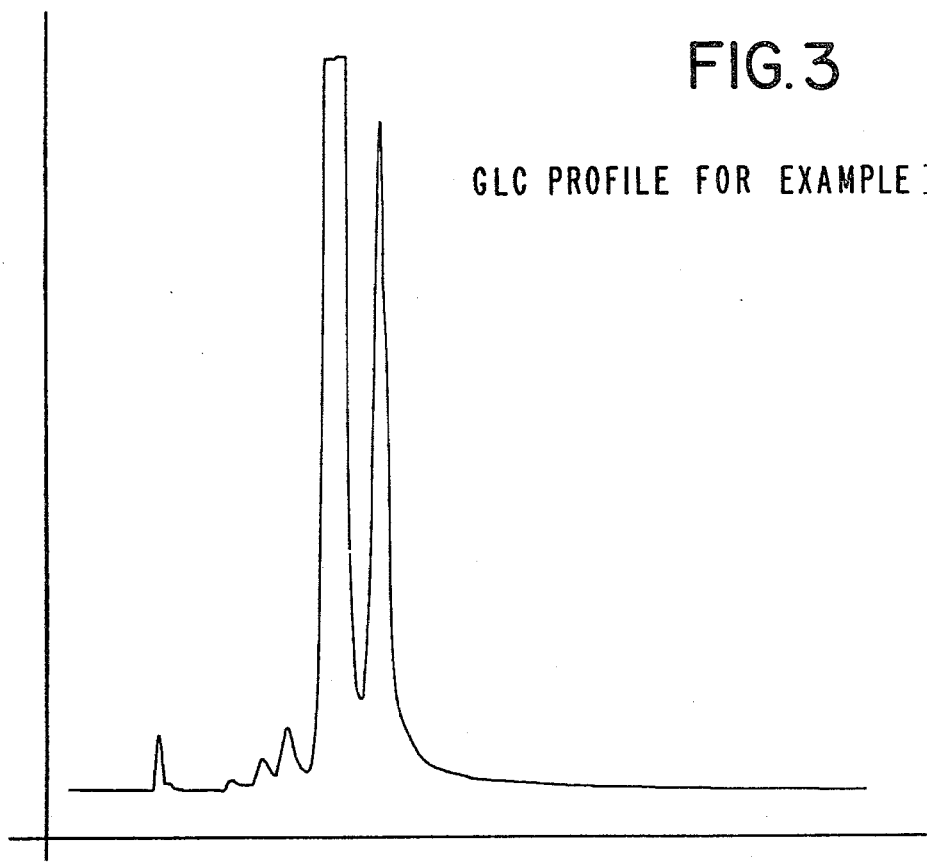

FIG. 3 represents the GLC profile for the reaction product of Example III.

Figure 4:
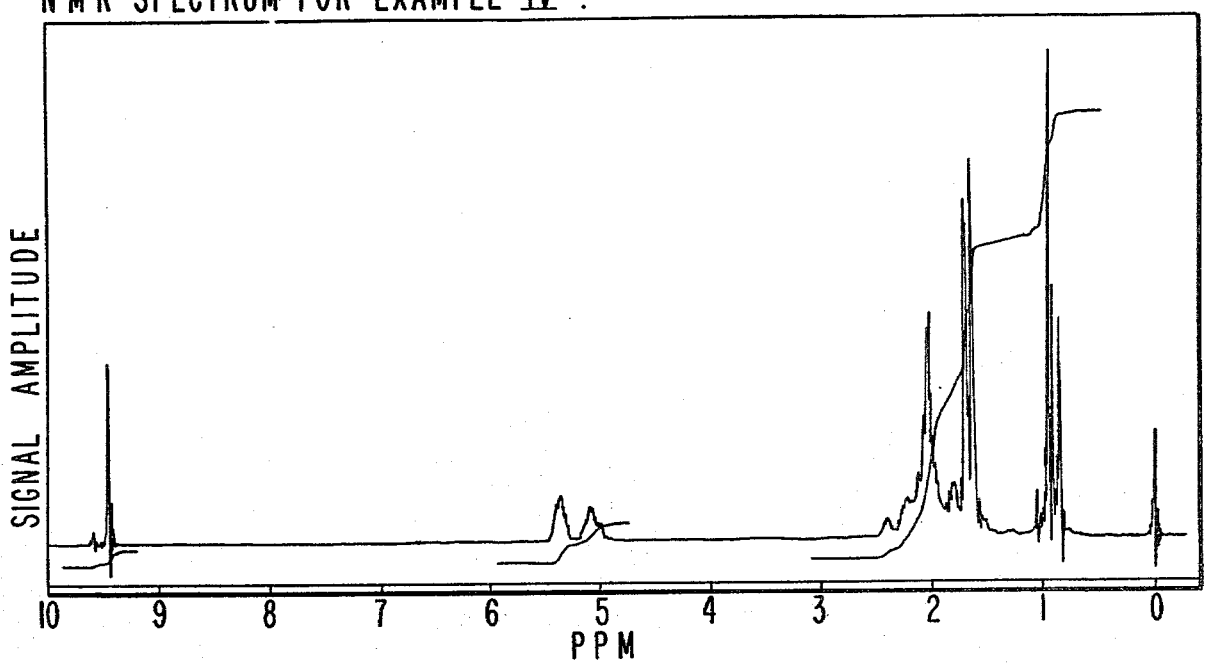

FIG. 4 represents the NMR spectrum for the aldehyde produced according to Example IV, having the structure:

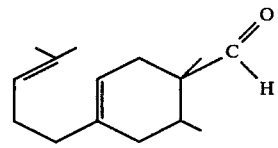

FIG. 5 represents the infra-red spectrum for the aldehyde having the structure:

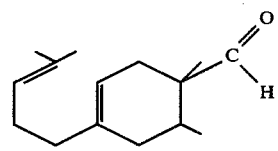

produced according to Example IV.

FIG. 6 represents the NMR spectrum for the mixture of aldehydes produced according to Example V, having the generic structure:

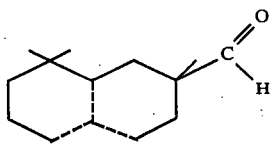

FIG. 7 represents the infra-red spectrum for the mixture of aldehydes produced according to Example V, having the generic structure:

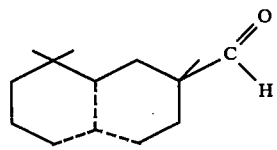

wherein one of the dashed lines represents a carbon-carbon double bond and the other of the dashed lines represents carbon-carbon single bonds.

FIG. 8 represents the GLC profile for the product produced according to Example V, containing the aldehydes having the generic structure:

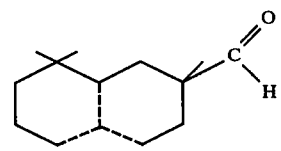

Figure 9:
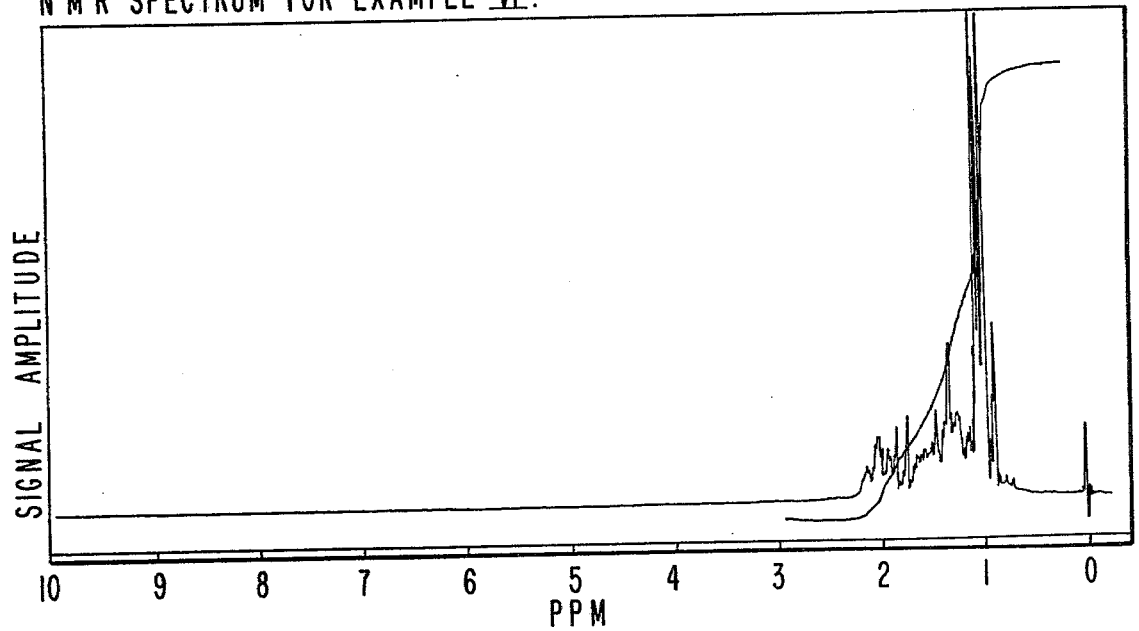

FIG. 9 represents the NMR spectrum for the tricyclic ketone having the structure:

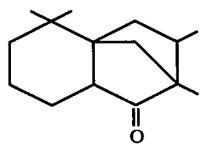

produced according to Example VI.

Figure 10:
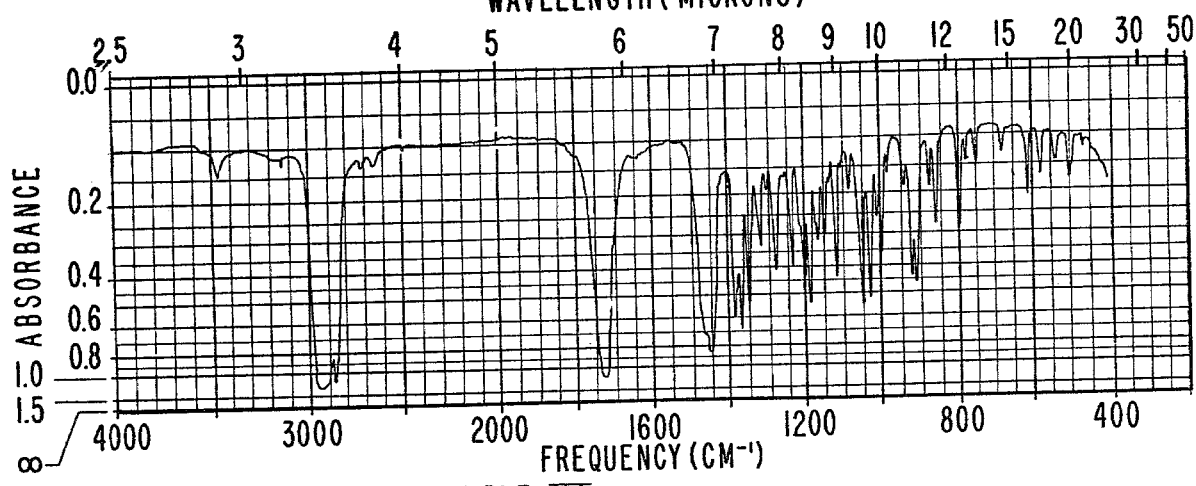

FIG. 10 represents the infra-red spectrum for the tricyclic ketone having the structure:

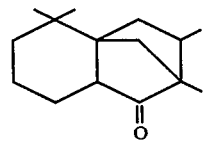

produced according to Example VI.

Figure 11:
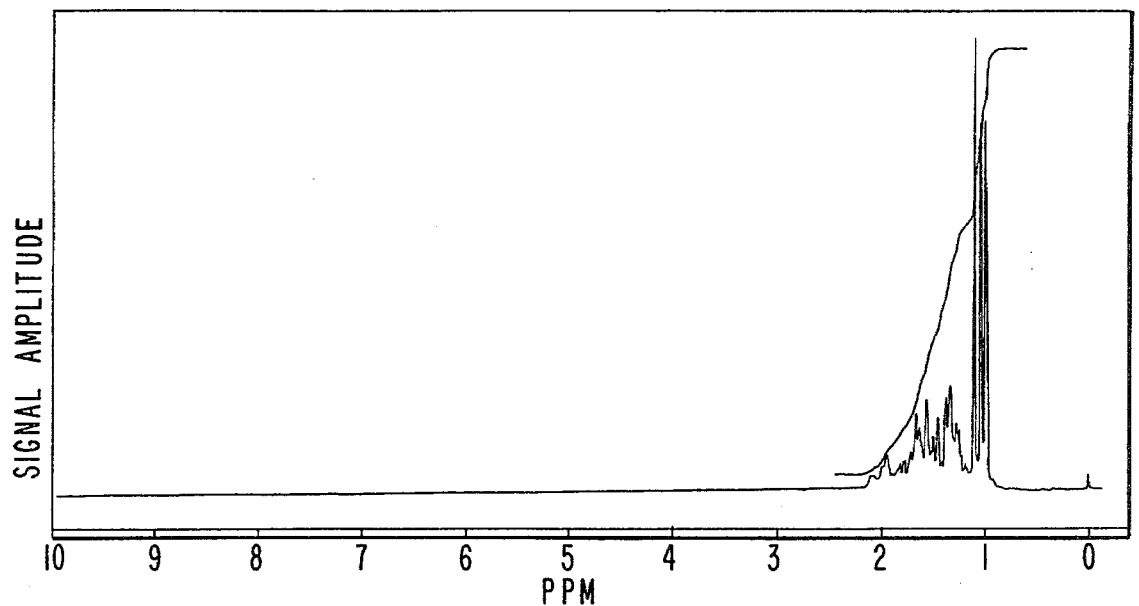

FIG. 11 represents the NMR spectrum for the tricyclic ketone produced according to Example VII, having the structure:

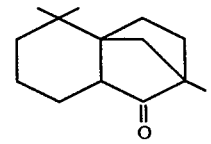

Figure 12:
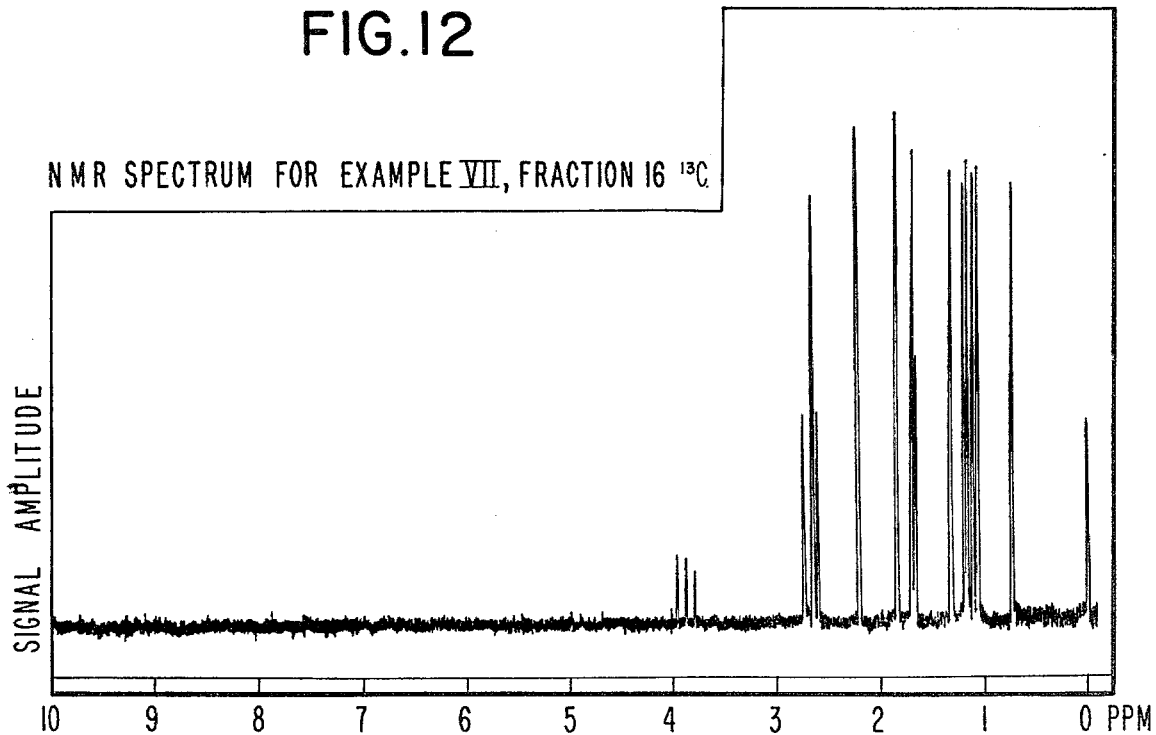

FIG. 12 represents the $^{13}C$ NMR spectrum for the tricyclic ketone having the structure:

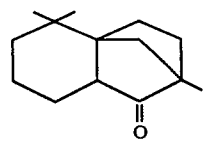

produced according to Example VII.

FIG. 13 represents the NMR spectrum for the tricyclic ketone having the structure:

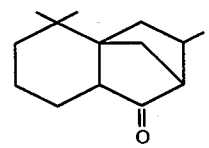

produced according to Example VIII.

FIG. 14 represents the infa-red spectrum for the tricyclic ketone having the structure:

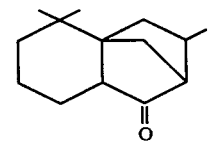

produced according to Example VIII.

THE INVENTION

It has now been discovered that novel smoking tobacco and smoking tobacco flavoring compositions having sweet, floral, woody, spicy, leathery and/or amber aroma and taste nuances prior to smoking and sweet natural tobacco tastes and aromas on smoking both in the main stream and the side stream, as well as novel perfume compositions, colognes and perfumed articles (e.g., solid or liquid anionic, cationic and nonionic detergent compositions, as well as dryer-added fabric softener articles, as well as cosmetic powders) having intense and pleasant oily, woody amber, leathery, warm spice, earthy camphoraceous, patchouli-like, balsamic, green, cardamom-like, vetiver-like, sweet woody, amber and minty aromas may be provided by the utilization of one or more tricyclic ketone derivatives having the generic structure:

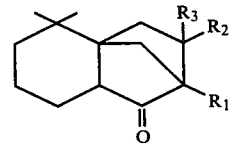

wherein each of $R_1$, $R_2$ and $R_3$ are the same or different and each represents hydrogen or C1–C3 lower alkyl, such as methyl, ethyl, n-propyl and i-propyl.

The novel tricyclic ketones of our invention useful as indicated supra, may be produced preferably by one of the following processes:

(1) First reacting myrcene having the structure:

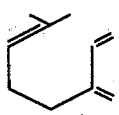

with an alpha, beta unsaturated aldehyde having the generic structure:

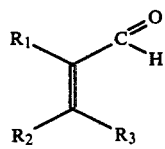

wherein $R_1$, $R_2$ and $R_3$ are the same or different hydrogen or lower alkyl in the presence of a Lewis acid catalyst such as aluminum trichloride, boron trifluoride, stannic fluoride, zinc fluoride zinc bromide, ethyl aluminum dichloride or diethyl aluminum monochloride or, in the absence of catalysts under conditions of higher temperatures, 50°–150° C., to produce an unsaturated aldehyde or a mixture of unsaturated aldehydes having the generic structure:

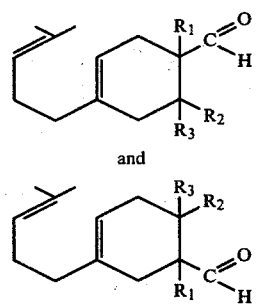

Depending upon the catalyst used, the proportion of one isomer to the other isomer of resulting aldehyde will vary.

The aldehydes having the generic structures:

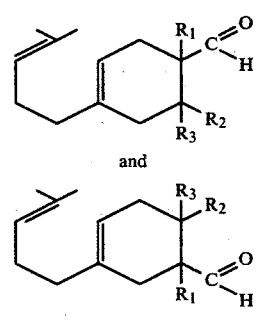

are either separated by standard means of physical separation, e.g., fractional distillation or industrial column chromatography, or they are permitted to remain as a mixture. These aldehydes are then reacted in the presence of acid, such as phosphoric acid or sulfuric acid, in order to produce cyclic aldehydes having the generic structure:

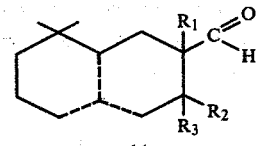

and/or

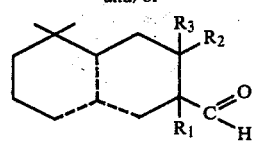

wherein one of the dashed lines represents a carbon-carbon double bond and each of the other dashed lines represents carbon-carbon single bonds, and wherein $R_1$, $R_2$ and $R_3$ are the same or different hydrogen or C1–C3 lower alkyl.

When the aldehyde having the structure:

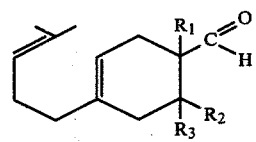

is reacted alone, the resulting aldehyde has the generic structure:

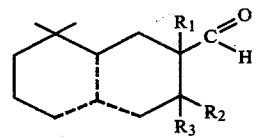

and is, of course, a mixture of aldehydes. Insofar as our invention is concerned, the only useful aldehyde to be reacted for producing compounds having the generic structure:

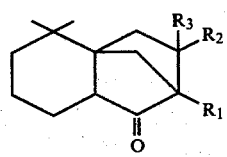

is the aldehyde having the structure:

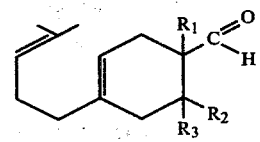

This aldehyde will form the mixture of aldehydes having the structure:

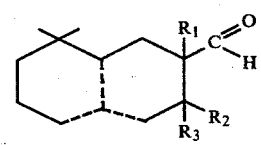

which in turn is reacted under acid conditions, (either Lewis acid or mineral acid) to form the tricyclic ketone having the structure:

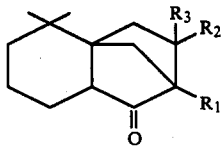

according to the mechanism:

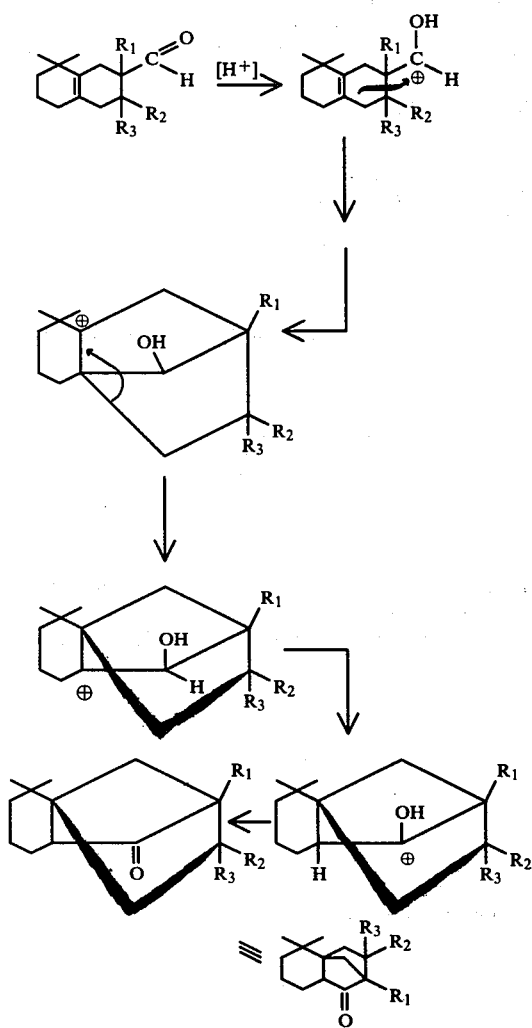

In the alternative, the aldehyde having the structure:

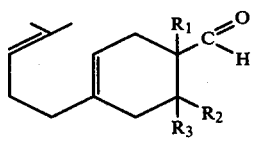

may first be reacted with an amine R'NH₂ to form an imine having the generic structure:

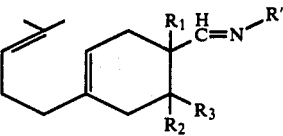

which in turn is cyclized in the presence of mineral acid or Lewis acid to form the mixtures of compounds having the structures:

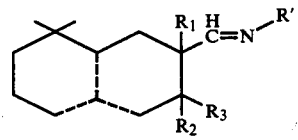

wherein R' is lower alkyl and $R_1$, $R_2$ and $R_3$ are the same or different hydrogen or lower alkyl and one of the dashed lines is a carbon-carbon double bond and each of the other dashed lines represents carbon-carbon single bonds.

The resulting mixture of aldehydes having the structure:

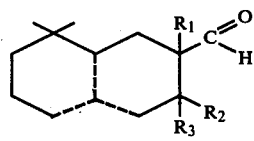

but not the mixture of aldehydes having the structure:

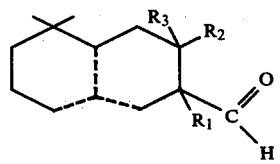

or the resulting imine having the structure:

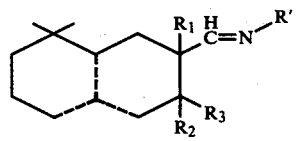

is thus reacted to form the novel compounds of our invention having the structure:

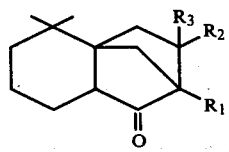

in the presence of acid.

The condition for the Diels-Alder reaction between myrcene, having the structure:

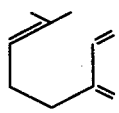

and the alpha, beta unsaturated aldehyde, having the structure:

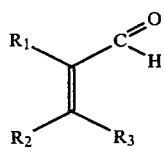

as well as the conditions for the reaction of the compounds having the structures:

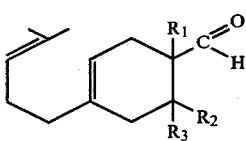

and

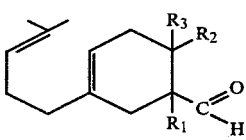

to form the cyclic compounds having the structures:

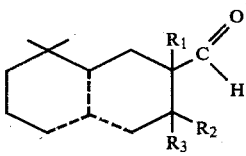

and

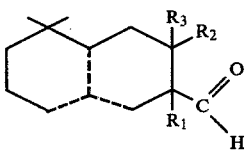

as set forth in the literature as follows:
1. U.S. Pat. No. 3,911,018 issued on Oct. 7, 1975, at Columns 7, 8 and 9 thereof.
2. U.S. Pat. No. 2,933,506 issued on Apr. 19, 1960, at Examples 1, 2 and 3 at Columns 6, 7 and 8 thereof.

In the reaction to form the tricyclic ketone having the structure:

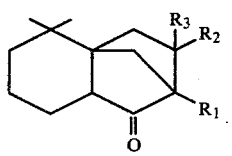

from the aldehyde having the structure:

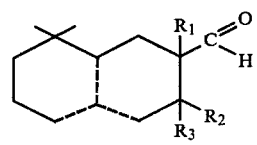

the mineral acids which can be used are hydrochloric acid, sulfuric acid, phosphoric acid, or paratoluene sulfonic acid. An inert solvent is used in this reaction, xylene, toluene, benzene or diethylbenzene, or a chlorocarbon such as chloroform ($CHCl_3$) or methylene chloride ($CH_2Cl_2$).

The mole ratio of aldehyde having the structure:

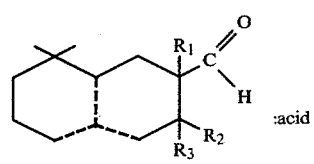 :acid may vary from 1:10 up to 10:1 with a range of mole ratios of from about 1:2 up to about 1:0.5 being preferred.

The temperature of reaction may vary from 25° C. up to 100° C. with a temperature range from about 60° C. up to about 80° C. being preferred.

In place of the mineral acid being used, a Lewis acid may be used, such as aluminum chloride, stannic chloride, titanium tetrachloride, boron trifluoride, or boron trifluoride etherate, ethyl aluminum chloride, ethyl aluminum dichloride, zinc bromide or zinc chloride. The temperature of reaction may vary from 25° C. up to 100° C. with a temperature of from 25° C. to 45° C. being preferred. The mole ratio of aldehyde having the structure:

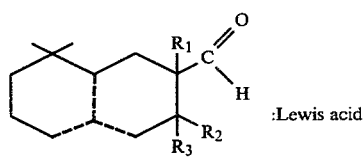 :Lewis acid may vary from 1:1 up to 1:2 with an inert solvent being used which is either toluene, benzene, xylene, diethylbenzene, chloroform or methylene chloride.

The time of reaction for forming of the compounds represented by the generic structure:

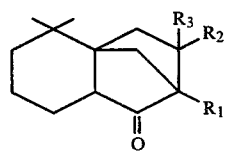

using the compounds represented by the generic structure:

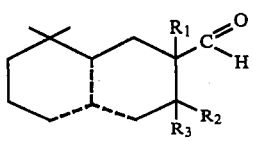

may vary from about 1 hour up to about 12 hours when operating at reflux temperatures, such as 110°–120° C., using a toluene solvent. Preferred is a reaction time of between 5 and 12 hours.

It is noteworthy that whereas the genus of compounds having the structure:

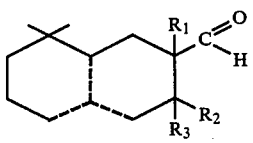

will react to form the genus of compounds having the structure:

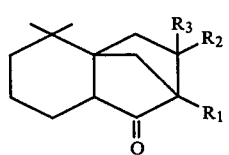

the genus of compounds having the structure:

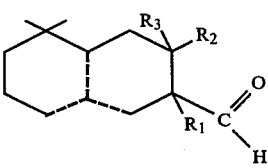

will not so react when treated with either Lewis acid or mineral acid under high temperature conditions. This gives rise to the advantage of separating out the isomeric components of compounds having the structures:

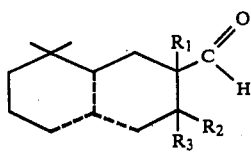

and

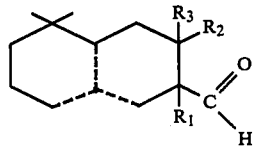

or compounds having the structures:

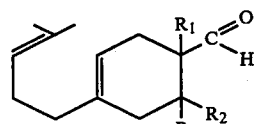

and

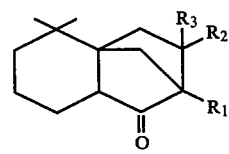

Examples of the tricyclic ketone compounds having the generic structure:

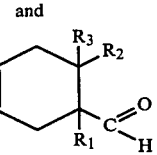

produced according to the processes of our invention and their organoleptic properties are set forth in the following table:

TABLE I

| STRUCTURE | NAME OF COMPOUND | PERFUMERY EVALUATION | SMOKING TOBACCO FLAVOR EVALUATION |
|---|---|---|---|
| 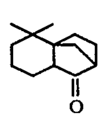 | hexahydro-5,5-dimethyl-2H-2,4-a-methanonaphthalene-1(5H)-one | A sweet, woody, camphoraceous aroma with minty and ambery nuances. |  |

TABLE I-continued

| STRUCTURE | NAME OF COMPOUND | PERFUMERY EVALUATION | SMOKING TOBACCO FLAVOR EVALUATION |
|---|---|---|---|
| 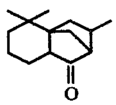 | hexahydro-2,5,5-trimethyl-2H-2,4-a-methanonaphthalene-1(5H)-one | A low-keyed, oily, woody, amber aroma with woody and slightly leathery undertones. On purification a deep woody, earthy camphoraceous, patchouli-like aroma with amber and leathery undertones. | Prior to smoking a sweet, floral, musty, woody, spicy and leathery and amber-like aroma and taste. On smoking, a sweet, floral, musty, woody, spicy, leathery, amber-like aroma with a slight cooling effect in both the main stream and the side stream. When added to a filter, a sweet aroma with enhanced tobacco taste and aroma of a very natural quality is obtained in the main stream and the side stream. |
| 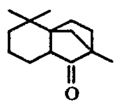 | hexahydro-1,5,5-trimethyl-2H-2,4-a-methanonaphthalene-1(5H)-one | A woody aroma with green, tart, cardamom-like undertones. | |
| 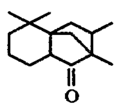 | hexahydro-1,2,5,5-tetramethyl-2H-2,4-a-methanonaphthalene-1(5H)-one | A sweet woody, camphoraceous, balsamic aroma with patchouli and deep woody undertones. | A floral ionone-like aroma with woody, balsamic nuances prior to and on smoking both in the main stream and the side stream. |

One or more of the tricyclic ketones of our invention and one or more auxiliary perfume ingredients including, e.g., alcohols, aldehydes, ketones other than the tricyclic ketones of our invention, terpenic hydrocarbons, nitriles, esters, lactones, natural essential oils and synthetic essential oils, may be admixed so that the combined odors of the individual components produce a pleasant and desired fragrance, particularly in the woody, ambery, leathery, patchouli-like and vetiver fragrances. Such perfume compositions usually contain (a) the main note or the "bouquet" or foundation stone of the composition; (b) modifiers which round off and accompany the main note; (c) fixatives which include odorous substances which lead a particular note to the perfume throughout all stages of evaporation and substances which retard evaporation; and (d) topnotes which are usually low boiling fresh smelling materials.

In perfume compositions, it is the individual components which contribute to their particular olfactory characteristics, however the over-all sensory effect of the perfume composition will be at least the sum total of the effects of each of the ingredients. Thus, one or more tricyclic ketone derivative(s) of our invention can be used to alter, modify or enhance the aroma characteristics of a perfume composition, for example, by utilizing or moderating the olfactory reaction contributed by another ingredient in the composition.

The amount of tricyclic ketone derivative(s) of our invention which will be effective in perfume compositions as well as in perfumed articles and colognes depends on many factors, including the other ingredients, their amounts and the effects which are desired. It has been found that perfume compositions containing as little as 0.01% of tricyclic ketone derivative(s) or even less (e.g., 0.005%) can be used to impart a vetiver aroma with sweet woody, citrusy, musky, woody/peppery, woody/leathery, hay and green nuances to soaps, cosmetics, detergents, powders and colognes. The amount employed can range up to 70% of the fragrance components and will depend on considerations of cost, nature of the end product, the effect desired on the finished product and the particular fragrance sought.

The tricyclic ketone derivative(s) of our invention are useful [taken along or together with other ingredients in perfume compositions] as (an) olfactory component(s) in detergents and soaps, space odorants and deodorants, perfumes, colognes, toilet water, bath preparations, such as lacquers, brilliantines, pomades and shampoos; cosmetic preparations, such as creams, deodorants, hand lotions and sun screens; powders, such as talcs, dusting powders, face powders and the like. When used as (an) olfactory component(s) as little as 1% of tricyclic ketone derivative(s) will suffice to impart intense oily, woody amber, leathery, warm spice, earthy camphoraceous, patchouli-like, balsamic, green, cardamon-like, vetiver-like, sweet woody, ambery and minty aromas to various formulations such as vetiver formulations. Although, generally, no more than 60% of the tricyclic ketone derivative(s), based on the ultimate end product, is required in the perfume composition, amounts of tricyclic ketone derivative(s) of up to 95% may be used in such perfume composition.

When used in perfumed articles such as anionic, cationic and non-ionic detergents, or dryer-added fabric softener articles, cosmetic powders or deodorant compositions, from 0.1% up to 5.0% by weight of the tricyclic ketone based on the over-all perfumed article weight may be used in the perfumed articles to impart intense oily, woody amber, leathery, warm spice, earthy camphoraceous, patchouli-like, balsam-like, green, cardamom-like, vetiver-like, sweet woody, amber and minty aromas.

In addition, the perfume composition or fragrance composition of our invention can contain a vehicle, or carrier for the tricyclic ketone derivative(s). The vehicle can be a liquid such as a non-toxic alcohol, a non-toxic glycol, or the like. The carrier can also be an absorbent solid, such as a gum (e.g., gum arabic) or components for encapsulating the composition (such as gelatin).

An additional aspect of our invention provides an organoleptically improved smoking tobacco product and additives therefor, as well as methods of making the same which overcome problems heretofore encountered in which specific sweet, floral, woody, spicy, leathery and amber flavor characteristics of natural smoking tobacco (prior to and on smoking in both the mainstream and the sidestream) as well as cooling effects, are created, enhanced, modified or augmented and may be readily controlled and maintained at the desired uniform level regardless of variations in the tobacco components of the blend.

In carrying out this aspect of our invention, we add to smoking tobacco compositions or a suitable substitute therefor (e.g., dried lettuce leaves), or we add to the wrapper used in producing smoking tobacco articles which surround a cylindrical formed body of smoking tobacco, or we add to the filter which is in intimate contact with both the wrapper and the cylindrical shaped body of tobacco, an aroma and flavor additive containing as an active ingredient one or more of the tricyclic ketones of our invention.

In addition to the tricyclic ketone(s) of our invention other flavoring and aroma additives may be added to the smoking tobacco material or substitute therefor either separately or in mixture with the ketone(s) as follows:

I. Synthetic Materials:

Beta-ethyl-cinnamaldehyde;
Eugenol;
Dipentene;
Damascenone;
Maltol;
Ethyl maltol;
Delta undecalactone;
Delta decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-one;
2-Methyl-5-isopropylacetophenone;
2-Hydroxy-2,5,5,8a-tetramethyl-1-(2-hydroxyethyl)-decahydronaphthalene;
Dodecahydro-3a,6,6,9a-tetramethylnaphtho-(2,1-b)-furan
4-Hydroxyhexanoic acid, gamma lactone; and
Polyisoprenoid hydrocarbons defined in Example V of U.S. Pat. No. 3,589,372 issued on June 29, 1971.

II. Natural Oils:

Celery seed oil;
Coffee extract;
Bergamot Oil;
Cocoa extract;
Nutmeg Oil; and
Origanum Oil.

An aroma and flavoring concentrate containing one or more tricyclic ketone derivative(s) of our invention and, if desired, one or more of the above indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as enhancement or the imparting of natural and/or sweet notes and/or cooling notes and/or floral, woody, spicy, leathery or amber notes, we have found that satisfactory results are obtained if the proportion by weight of the sum total of tricyclic ketone derivative(s) to smoking tobacco material is between 50 ppm and 1,500 ppm (0.015%–0.15%). We have further found that satisfactory results are obtained if the proportion by weight of the sum total of tricyclic ketone derivative(s) used to flavoring material is between 1,500 and 15,000 ppm (0.15%–1.5%).

Any convenient method for incorporating the tricyclic ketone derivative(s) into the tobacco product may be employed. Thus, the tricyclic ketone derivative(s) taken alone or along with other flavoring additives may be dissolved in a suitable solvent such as ethanol, diethyl ether and/or volative organic solvents and the resulting solution may either be spread on the cured, cased and blended tobacco material or the tobacco material may be dipped into such solution. Under certain circumstances, a solution of the tricyclic ketone derivative(s) taken alone or taken further together with other flavoring additives as set forth above, may be applied by means of a suitable applicator such as a brush or roller on the paper or leaf wrapper for the smoking product, or it may be applied to the filter by either spraying, or dipping, or coating.

Furthermore, it will be apparent that only a portion of the tobacco or substitute therefor need be treated and the thus treated tobacco may be blended with other tobaccos before the ultimate tobacco product is formed. In such cases, the tobacco treated may have the tricyclic ketone derivative(s) in excess of the amounts or concentrations above indicated so that when blended with other tobaccos, the final product will have the percentage within the indicated range.

In accordance with one specific example of our invention, an aged, cured and shredded domestic burley tobacco is sprayed with a 20% ethyl alcohol solution of hexahydro-2,5,5-trimethyl-2H-2,4-a-methanonaphthalene-1(5H)-one having the structure:

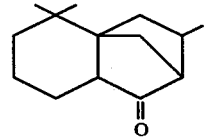

in an amount to provide a tobacco composition containing 800 ppm by weight of hexahydro-2,5,5-trimethyl-2H-2,4-a-methanonaphthalene-1(5H)-one one a dry basis. Thereafter, the alcohol is removed by evaporation and the tobacco is manufactured into cigarettes by the usual techniques. The cigarette when treated as indicated has a desired and pleasant aroma which is detectable in the main and sidestreams when the cigarette is smoked. The aroma is described as being sweeter, more aromatic, more tobacco-like and having sweet, woody, amber notes.

While our invention is particularly useful in the manufacture of smoking tobacco, such as cigarette tobacco, cigar tobacco and pipe tobacco, other tobacco products, formed from sheeted tobacco dust or fines may also be used. Likewise, the tricyclic ketone derivative(s) of our invention can be incorporated with materials such as filter tip materials (e.g., cellulose acetate filters wherein sweet, woody, piney and/or cooling effects are desired), seam paste, packaging materials and the like which are used along with tobacco to form a product adapted for smoking. Furthermore, the tricyclic ketone derivative(s) can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco plant parts or substitute materials or both.

It will thus be apparent that the tricyclic ketone(s) of our invention can be utilized to alter, modify or enhance sensory properties, particularly organoleptic properties, such as flavor(s) and/or fragrance(s) of a wide variety of consumable materials, such as smoking tobacco, perfumed articles and perfumed compositions in colognes.

The following examples serve to illustrate processes for specifically producing the tricyclic ketone(s) of our invention and processes for utilizing said tricyclic ketone(s) for their organoleptic properties.

All parts and percentages given herein are by weight unless otherwise specified.

EXAMPLES I-IX

The following examples set forth specific embodiments of the reaction scheme:

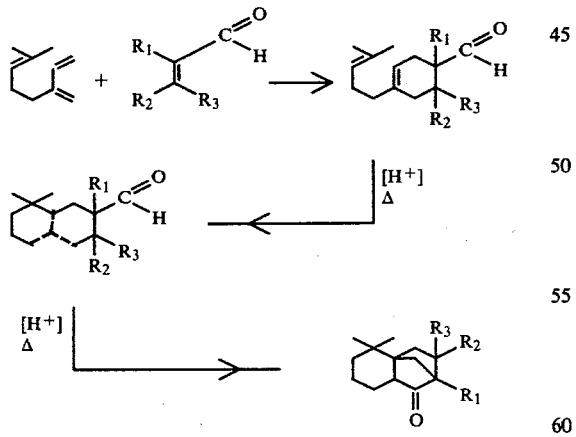

wherein $R_1$, $R_2$ and $R_3$ are each the same or different and each represents hydrogen or lower alkyl, and one of the dashed lines represents a carbon-carbon double bond and each of the other dashed lines represent carbon-carbon single bonds.

The reactions can also be carried out according to the following reaction scheme:

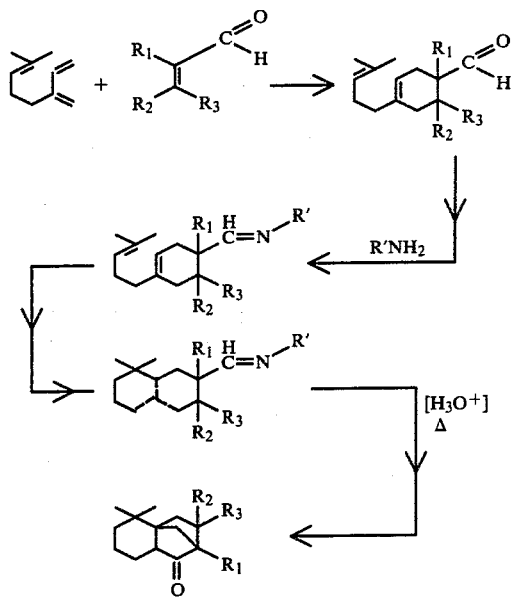

EXAMPLE I

PREPARATION OF A MIXTURE OF 1,2,3,4-TETRAHYDRO-8,8-DIMETHYL-2-TETRALINCARBOXALDEHYDE and HEXAHYDRO-5,5-DIMETHYL-2H-2,4-a-METHANONAPHTHALENE-1(5H)-ONE Reaction:

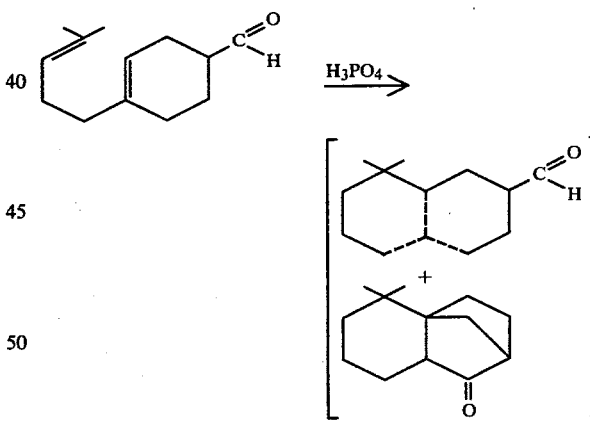

1200 grams of Myrac Aldehyde ® (trademark of the Givaudan Company of Delawanna, NJ) (4-(4-methyl-3-pentenyl)-3-cyclohexenecarboxaldehyde) and is added dropwise with stirring at 45° C. over a 4 hour period to a mixture of 600 grams of toluene and 1200 grams of 85% phosphoric acid. At the end of the addition the reaction mass is stirred for an additional 30 minutes and then poured into 5 l of water. The mass is stirred and the organic layer is further washed twice with 2 liters of saturated salt solution. The pH during the second wash is adjusted to pH8 with sodium carbonate. The organic layer is distilled through a short column to afford 1009 grams of crude product. Fractional redistillation through a 1½"×12" Goodloe packed column affords 911 grams of purified product (b.p. 94° C., 3 mm). GLC analysis (200° C., isothermal, 10% SE-30 packed column) indicates a composition of 95%, 8,8-dimethyl-2-tetralincarboxaldehyde and 5% hexahydro-5,5-dimethyl-2H-2,4-a-methanonaphthalene-1(5H)-one.

FIG. 1 shows the nmr spectrum of hexahydro-5,5-dimethyl-2H-2,4-a-methanonaphthalene-1(5H)-one.

FIG. 2 shows the IR spectrum of hexahydro-5,5-dimethyl-2H-2,4-a-methanonaphthalene-1(5H)-one.

EXAMPLE II

PREPARATION OF A MIXTURE OF 1,2,3,4-TETRAHYDRO-8,8-DIMETHYL-2-TETRALINCARBOXALDEHYDE and

HEXAHYDRO-5,5-DIMETHYL-2H-2,4-a-METHANONAPHTHALENE-1(5H)-ONE

Reaction:

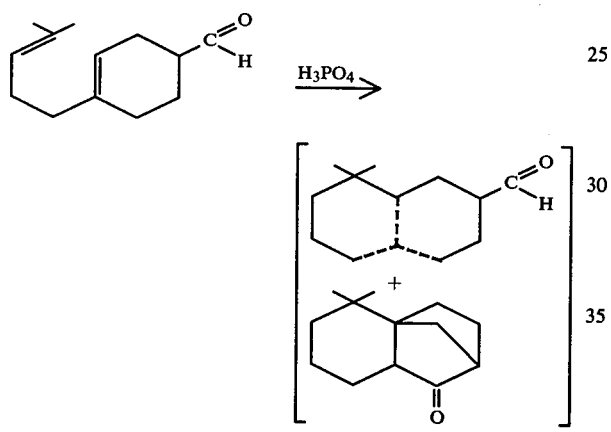

A mixture of 31.2 Kg of 85% phosphoric acid and 15.6 Kg of toluene are charged to a glass lined 50 gallon reactor and heated to 40° C. Myrac Aldehyde ® (31.4 Kg) is added with stirring over a four hour period at 40° C. After stirring the mass at 40° C. for 15 minutes, it is poured with stirring into a 100 gallon glass lined reactor containing 292 Kg of 15% salt solution. The layers are separated with heat and the organic phase is washed with salt water, 5% caustic solution, and salt water, respectively. The toluene is distilled from the organic mass at reduced pressure 50-100 psi. 150 grams of triethylamine, 75 grams of IONOL ® (a registered trademark of the Shell Chemical Company; butylated hydroxy toluene), and 75 grams of PRIMOL ® (a registered trademark identifying a hydrocarbon mineral oil produced by Exxon Incorporation of Linden, NJ) are added to the mass. Quick distillation through a short column affords 22.2 Kg of crude product. Fractional redistillation through a 3"×24" Goodloe packed column affords 20.6 Kg of product (b.p. 94° C., 3 mm.) GLC analysis (100°-200°, 8°/min., ¼"×8'10% Carbowax packed column) indicates 96% 1,2,3,4-tetrahydro-8,8-dimethyl-2-tetralincarboxaldehydes and 4% hexahydro-5,5-dimethyl-2H-2,4-a-methanonaphthalene-1(5H)-one.

EXAMPLE III

PREPARATION OF HEXAHYDRO-5,5-DIMETHYL-2H-2,4-a-METHANONAPHTHALENE-1(5H)-ONE AND A MIXTURE CONSISTING OF 1,2,3,4-TETRAHYDRO-8,8-DIMETHYL-2-TETRALINCARBOXALDEHYDE and

HEXAHYDRO-5,5-DIMETHYL-2H-2,4-a-METHANONAPHTHALENE-1(5H)-ONE

Reaction:

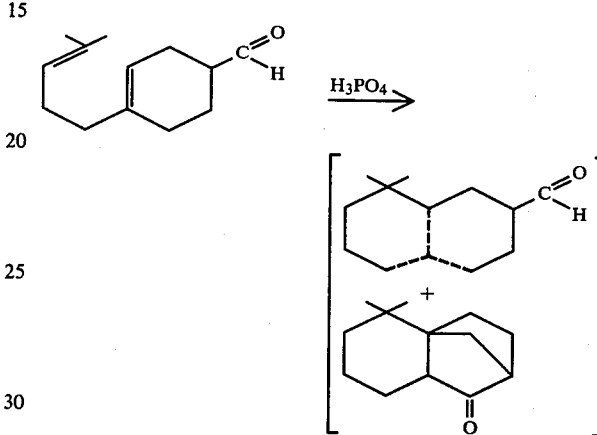

A mixture of 30.9 Kg of 85% phosphoric acid and 15.5 Kg of toluene is charged to a glass lined 50 gallon reactor and heated to 60° C. Myrac Aldehyde ® (30.9 Kg) is added with stirring over a 4 hour period. The reaction mass is processed as in Example II. Distillation through a 3"×24" Goodloe packed column affords 25 Kg of product consisting overall of 75% 1,2,3,4-tetrahydro-8,8-dimethyltetralin and 25% of hexahydro-5,5-dimethyl-2H-2,4-a-methanonaphthalene-1(5H)-one. Refractionation using a reflux to take off ratio of 9:1 affords decahydro-hexahydro-5,5-dimethyl-2H-2,4-a-methanonaphthalene-1(5H)-one.

FIG. 3 represents the GLC trace of the crude reaction mixture, after removal of toluene and before distillation (220° C. isothermal, ¼"×8' 10% Carbowax packed column).

EXAMPLE IV

PREPARATION OF 1,6-DIMETHYL-4-(4-METHYL-3-PENTENYL)-3-CYCLOHEXENE-1-CARBOXALDEHYDE

Reaction:

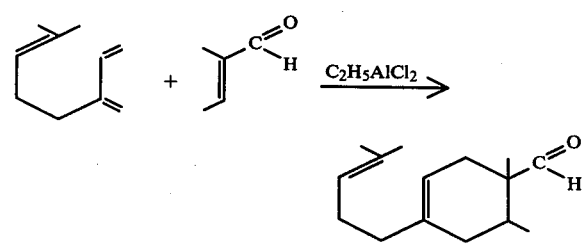

A 3-neck reaction vessel is charged with 100 ml benzene and 50 grams of 25% ethyl aluminum dichloride in benzene. A solution containing 320 grams myrcene (85% pure), 170 grams 2-methyl-2-butenal, and 200 ml benzene is fed in at 40°–50° C. over a 1 hour period. The temperature is then raised to 60° C. and held there for ½ hour. An additional 10 grams ethyl aluminum dichloride solution mixed with 20 ml benzene is added and heating is continued for an additional ½ hour. The mixture is then cooled, water is added and the layers are separated. The organic layer is washed with water and distilled without fractionation to free the material of residue. Redistillation through an 18" Goodloe packed column provides 199 grams of 1,6-dimethyl-4-(4-methyl-3-pentenyl)-3-cyclohexene-1-carboxaldehyde (b.p. 105° C., 0.9 mm).

FIG. 4 represents the nmr spectrum of 1,6-dimethyl-4-(4-methyl-3-pentenyl)-3-cyclohexene-1-carboxaldehyde.

FIG. 5 represents the IR spectrum of 1,6-dimethyl-4-(4-methyl-3-pentenyl)-3-cyclohexene-1-carboxaldehyde.

EXAMPLE V

PREPARATION OF 1,2,3,4-TETRAHYDRO-2,3,8,8-TETRAMETHYL-2-TETRALINCARBOXALDEHYDE

Reaction:

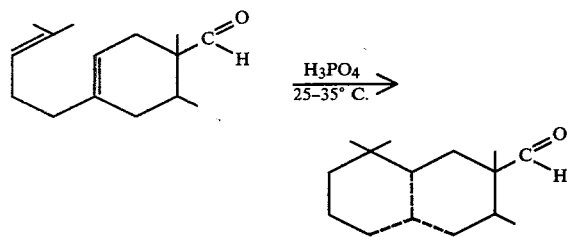

A 1-liter flask equipped with thermometer, mechanical stirrer and addition funnel is charged with 197 grams of 85% phosphoric acid (Mallinkrodt) and 49 grams toluene. The mixture is stirred at 25°–35° C. as 197 grams of the aldehyde as prepared in Example IV is added over 35 minutes. The mixture is then stirred for 5 hours at that temperature range at which time complete reaction is indicated by GLC (Carbowax column). Cooling is applied and 250 ml water is added. The resulting mixture is extracted twice with 500 ml portions of ether. The extracts are washed with 10% sodium hydroxide solution and then with water. The organic solution is dried over sodium sulfate and distilled to free the product from residue. The resulting oil is then fractionally distilled through a 5 ft. Vigreux column to give 92 grams of 1,2,3,4-tetrahydro-2,3,8,8-tetramethyl-2-tetralincarboxaldehyde (b.p. 113°–115° C., 2 mm).

FIG. 6 represents the nmr spectrum of 1,2,3,4-tetrahydro-2,3,8,8-tetramethyl-2-tetralincarboxaldehyde.

FIG. 7 represents the IR spectrum of 1,2,3,4-tetrahydro-2,3,8,8-tetramethyl-2-tetralincarboxaldehyde.

FIG. 8 represents the GLC trace of the tetrahydro-2,3,8,8-tetramethyl-2-tetralincarboxaldehyde isomers (100°–220° C., 8°/min., ¼"×10' 10% Carbowax packed column).

EXAMPLE VI

PREPARATION OF HEXAHYDRO-1,2,5,5-TETRAMETHYL-2H-2,4-a-METHANONAPHTHALENE-1(5H)-ONE

Reaction:

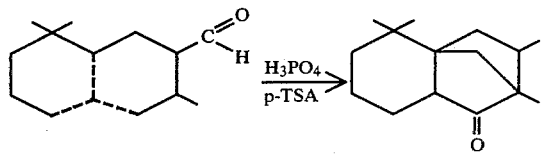

A 500 ml reaction flask is charged with 107 grams toluene, 107 grams 85% phosphoric acid, and 107 grams of 1,2,3,4-tetrahydro-2,3,8,8-tetramethyl-2-tetralincarboxaldehyde. The mixture is heated at reflux for 1.5 hours at which time 1.0 grams p-toluenesulfonic acid is added and reflux is continued for an additional 8.5 hours. The mixture is cooled, diluted with water, and 200 ml ether is added. The layers are separated and the organic layer is washed with water, 10% sodium bicarbonate, and again with water. After drying over magnesium sulfate the solvent is evaporated and the remaining material is distilled without fractionation. The obtained distillate is then fractionally distilled through a 5 foot Vigreux column to give 88 grams of product, b.p. 104°–109° C. (1.0–1.9 mm) consisting of 5% starting material and 95% hexahydro-1,2,5,5-tetramethyl-2H-2,4-a-methanonaphthalene-1(5H)-one.

FIG. 9 represents the nmr spectrum of hexahydro-1,2,5,5-tetramethyl-2H-2,4-a-methanonaphthalene-1(5H)-one.

FIG. 10 represents the I spectrum of hexahydro-1,2,5,5-tetramethyl-2H-2,4-a-methanonapthalene-1(5H)-one.

EXAMPLE VII

PREPARATION OF HEXAHYDRO-1,5,5-TRIMETHYL-2H-2,4-a-METHANONAPHTHALENE-1(5H)-ONE

Reaction:

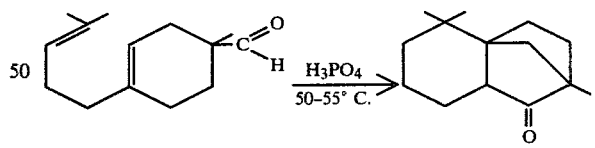

1-Methyl-4-(4-methyl-3-penten-1-yl)-3-cyclohexen-1-carboxaldehyde containing approximately 30% 1-methyl-3-(4-methyl-3penten-1-yl)-3-cyclohexen-1-carboxaldehyde (206 grams) is added in 35 minutes with good agitation to a mixture of toluene (200 ml) and 85% phosphoric acid (150 grams) at 50°–55° C. The mixture is stirred for 27 hours at 75°–85° C. The reaction mass is then washed with 1250 grams of 5% salt solution, and the aqueous layer is extracted with 100 mls of toluene. The combined organic phases are washed successively with 10% sodium carbonate solution and saturated salt solution. Distillation affords 37 grams of hexahydro-1,5,5-trimethyl-2H-2,4-a-methanonaphthalene-1(5H)-one.

FIG. 11 represents the nmr spectrum of hexahydro-1,5,5-trimethyl-2H-2,4-a-methanonaphthalene-1(5H)-one.

FIG. 12 represents the $^{13}$C nmr spectrum of hexahydro-1,5,5-trimethyl-2H-2,4-a-methanonaphthalene-1(5H)-one.

EXAMPLE VIII

PREPARATION OF HEXAHYDRO-2,5,5-TRIMETHYL-2H-2,4-a-METHANONAPHTHALENE-1(5H)-ONE

Reaction:

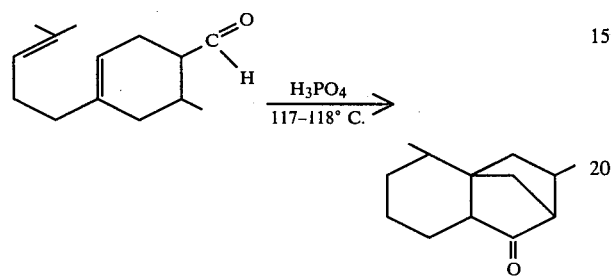

A mixture of 300 ml of toluene and 150 grams of 85% phosphoric acid is stirred at reflux while 618 grams of 6-methyl-4-(4-methyl-3-penten-1-yl)-3-cyclohexen-1-carboxaldehyde are added over a period of 30 minutes. The mixture is stirred for 11 hours and 117°–118° C. and then some of the toluene is distilled off to raise the reaction mixture to 135°–137° C. for an additional 2 hours. The mixture is then washed well and fractionally distilled through a 1½"×12" Goodloe packed column to give 160 grams of material which is shown by GLC analysis (220° C., isothermal, ¼"×10' 10% Carbowax packed column) to be greater than 92% hexahydro-2,5,5-trimethyl-2H-2,4-a-methanonaphthalene-1(5H)-one.

FIG. 13 represents the nmr spectrum of hexahydro-2,5,5-trimethyl-2H-2,4-a-methanonaphthalene-1(5H)-one.

FIG. 14 represents the IR spectrum of hexahydro-2,5,5-trimethyl-2H-2,4-a-methanonaphthalene-1(5H)-one.

EXAMPLE IX

PREPARATION OF HEXAHYDRO-1,5,5-TRIMETHYL-2H-2,4-a-METHANOPHTHALENE-1(5H)-ONE

Reaction:

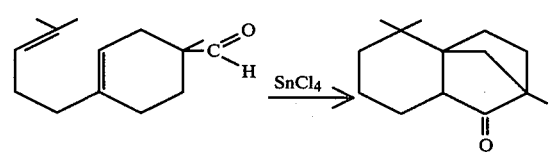

To a solution of 1-methyl-4-(4-methyl-3-penten-1-yl)-3-cyclohexene-1-carboxaldehyde (500 grams, 2.4 mol) and toluene (500 ml) is added stannic chloride (63 grams, 0.24 mol) dropwise at room temperature over a 10 minute period. The mass is heated to gentle reflux for 30 minutes, cooled to room temperature and stirred for an additional two hours. When the reaction is complete, the mass is poured into 1000 ml of 5% HCl solution and washed consecutively with 1000 ml of 5% aqueous sodium carbonate and 1000 ml of water. The organic layer is isolated and solvent removed under reduced pressure. The remaining mass is distilled throuh a 12"×2" silvered Goodloe column to afford a total of 209 grams of material, of which 73 grams is the desired product (b.p. 93°–94° C., 1.8 mm).

EXAMPLE X

PERFUME COMPOSITION

A perfume composition is prepared by admixing the following ingredients in the indicated proportions:

| Ingredient | Amount (Grams) |
|---|---|
| n-Decyl Aldehyde | 1 |
| n-Dodecyl Aldehyde | 2 |
| Methyl Nonyl Acetaldehyde | 0.5 |
| Linalool | 50 |
| Linalyl Acetate | 70 |
| Phenyl Ethyl Alcohol | 100 |
| Petitgrain SA | 20 |
| Bergamot Oil | 30 |
| Alpha Methyl Ionone | 25 |
| Mixture of isomers of 1',2',3',4', 5',6',7',8'-octahydro-2',3',8',8'-tetramethyl-2'-acetonaphthones produced by the process of Example II (prior to GLC separation) of U.S. Pat. No. 3,911,018 issued on October 7, 1975 | 10 |
| Cyclized Bicyclo C-12 material produced according to the process of Example IV of Canadian Patent 854,225 issued October 20, 1970 | 5 |
| Iso Bornyl Cyclohexyl Alcohol | 10 |
| Benzyl Acetate | 25 |
| 2-n-Heptyl Cyclopentanone | 5 |
| Hexahydro-2,5,5-trimethyl-2H-2,4-a-methanonaphthalene-1(5H)-one prepared according to Example VIII | 12.5 |
| TOTAL | 366.0 |

The foregoing blend is evaluated and found to have a high degree of richness and persistence in its novel amber and patchouli character. It has excellent unique leathery notes in addition to earthy notes contributed by the product produced according to Example VIII. This base composition can be admixed with aqueous ethanol, chilled and filtered to produce a finished cologne. The cologne so prepared has an amber aroma leading towards a woody amber, patchouli-like earthy note. The base composition can also be used to scent soap or other toilet goods such as lotion, aerosols, sprays and the like.

EXAMPLE XI

VETIVER FRAGRANCE

The following mixture is prepared:

| Ingredients | Parts by Weight |
|---|---|
| Hexahydro acetonaphthone derivative prepared according to Example III(B) of U.S. Pat. No. 4,108,799 issued on August 22, 1978 | 25 |
| Cedrol | 25 |
| Cedrenyl Acetate | 5 |
| Isobutyl Quinoline | 1 |
| Beta Ionone | 2 |
| Caryophyllene | 15 |
| Eugenol | 2 |
| Hexahydro-1,5,5-trimethyl-2H-2,4-a-Methanonaphthalene-1(5H)-one prepared | |

-continued

| Ingredients | Parts by Weight |
|---|---|
| according to Example IX | 25 |
| | 100 |

The hexahydro acetonaphthone derivative imparts the rich deep green woody note of vetiver to the vetiver fragrance. However, the hexahydro-1,5,5-trimethyl-2H-2,4-a-methanonaphthalene-1(5H)-one of Example IX imparts a varnishy, woody note of the vetiver family and, in addition, imparts a green, tart, cardamom-like note so important to rounding out this vetiver fragrance and making it more natural-like.

EXAMPLE XII

PREPARATION OF A COSMETIC POWDER

A cosmetic powder is prepared by mixing in a ball mill, 100 grams of talcum powder with 0.25 grams of one of the products listed below of our invention. The resulting material has an excellent perfume aroma as set forth in the table below:

TABLE II

| | DESCRIPTION OF COMPOSITION | FRAGRANCE CHARACTERISTICS |
|---|---|---|
| A. | Fragrance of Example X | amber, woody and earthy |
| B. | Fragrance of Example XI | vetiver with intense varnishy, woody note and excellent green, tart, cardamom-like nuances |
| C. | Hexahydro-5,5-dimethyl-2H-2,4-a-methanonaphthalene-2(5H)-one | sweet, woody, camphoraceous aroma with minty and ambery nuances |
| D. | Hexahydro-2,5,5-trimethyl-2H-2,4-a-methanonaphthalene-1(5H)-one | a low-keyed, oily, woody, amber aroma with woody and slightly leathery undertones. On purification a deep woody, earthy camphoraceous, patchouli-like aroma with amber and leathery undertones. |
| E. | Hexahydro-1,5,5-trimethyl-2H-2,4-a-methanonaphthalene-1(5H)-one | woody aroma with green, tart, cardamom-like undertones. |
| F. | Hexahydro-1,2,5,5-tetramethyl-2H-2,4-a-methanonaphthalene-1(5H)-one | sweet, woody, camphoraceous, balsamic aroma with patchouli and deep woody undertones. |

EXAMPLE XIII

PERFUMED LIQUID DETERGENT

Concentrated liquid detergents with aromas as set forth below (which detergents are produced from the Lysine salt of n-dodecyl benzene sulfonic acid, as more specifically described in U.S. Pat. No. 3,948,818, issued on Apr. 6, 1976) are prepared containing the tricyclic ketone derivatives and perfume compositions prepared, supra. They are prepared by adding and homogeneously mixing the appropriate quantity of tricyclic ketone derivative or perfume composition containing same in the liquid detergent. The detergents all possess excellent aromas as set forth in the table below:

TABLE II

| | DESCRIPTION OF COMPOSITION | FRAGRANCE CHARACTERISTICS |
|---|---|---|
| A. | Fragrance of Example X | amber, woody and earthy |
| B. | Fragrance of Example XI | vetiver with intense varnishy, woody note and excellent green, tart, cardamom-like nuances |
| C. | Hexahydro-5,5-dimethyl-2H-2,4-a-methanonaphthalene-2(5H)-one | sweet, woody, camphoraceous aroma with minty and ambery nuances |
| D. | Hexahydro-2,5,5-trimethyl-2H-2,4-a-methanonaphthalene-1(5H)-one | a low-keyed, oily, woody, amber aroma with woody and slightly leathery undertones. On purification a deep woody, earthy camphoraceous, patchouli-like aroma with amber and leathery undertones. |
| E. | Hexahydro-1,5,5-trimethyl-2H-2,4-a-methanonaphthalene-1(5H)-one | woody aroma with green, tart, cardamom-like undertones. |
| F. | Hexahydro-1,2,5,5-tetramethyl-2H-2,4-a-methanonaphthalene-1(5H)-one | sweet, woody, camphoraceous, balsamic aroma with patchouli and deep woody undertones. |

EXAMPLE XIV

PREPARATION OF A COLOGNE and

HANDKERCHIEF PERFUME

Perfume compositions and tricyclic ketone derivatives prepared, supra, as indicated in the table below are incorporated into colognes at concentrations of 1.5%, 2.0%, 2.5%, 3.0%, 3.5%, 4.0%, and 5.0% in 80%, 85%, 90% and 95% aqueous food grade ethanol; and into handkerchief perfumes at concentrations of 10%, 15%, 20%, 30%, 40% and 50% (in 90%, and 95% aqueous food grade ethanol). Distinct and definitive fragrance aromas as set forth in the table below are imparted to the colognes and to the handkerchief perfumes:

TABLE II

| | DESCRIPTION OF COMPOSITION | FRAGRANCE CHARACTERISTICS |
|---|---|---|
| A. | Fragrance of Example X | amber, woody and earthy |
| B. | Fragrance of Example XI | vetiver with intense varnishy, woody note and excellent green, tart, cardamom-like nuances |
| C. | Hexahydro-5,5-dimethyl-2H-2,4-a-methanonaphthalene-2(5H)-one | sweet, woody, camphoraceous aroma with minty and ambery nuances |
| D. | Hexahydro-2,5,5-trimethyl-2H-2,4-a-methanonaphthalene-1(5H)-one | a low-keyed, oily, woody, amber aroma with woody and slightly leathery undertones. On purification a deep woody, earthy camphoraceous, patchouli-like aroma with amber and leathery undertones. |
| E. | Hexahydro-1,5,5-trimethyl-2H-2,4-a-methanonaphthalene-1(5H)-one | woody aroma with green, tart, cardamom-like undertones. |
| F. | Hexahydro-1,2,5,5-tetramethyl-2H-2,4-a-methanonaphthalene-1(5H)-one | sweet, woody, camphoraceous, balsamic aroma with patchouli and deep woody undertones. |

EXAMPLE XV

PREPARATION OF SOAP COMPOSITION

One hundred grams of soap chips (obtained from Ivory ® Soap) (a trademark of Proctor & Gamble Company of Cincinnati, Ohio) are mixed with two grams of the materials as set forth in the table below until a substantially homogeneous composition is obtained. The resulting composition is melted at 180° C. for a period of 4 hours under 8 atmospheres nitrogen pressure. The resulting melt is cooled and formed into a soap bar. Each of the soap bars has an aroma as set forth in the table below:

TABLE II

| DESCRIPTION OF COMPOSITION | FRAGRANCE CHARACTERISTICS |
|---|---|
| A. Fragrance of Example X | amber, woody and earthy |
| B. Fragrance of Example XI | vetiver with intense varnishy, woody note and excellent green, tart, cardamom-like nuances |
| C. Hexahydro-5,5-dimethyl-2H-2,4-a-methanonaphthalene-2(5H)-one | sweet, woody, camphoraceous aroma with minty and ambery nuances |
| D. Hexahydro-2,5,5-trimethyl-2H-2,4-a-methanonaphthalene-1(5H)-one | a low-keyed, oily, woody, amber aroma with woody and slightly leathery undertones. On purification a deep woody, earthy camphoraceous, patchouli-like aroma with amber and leathery undertones. |
| E. Hexahydro-1,5,5-trimethyl-2H-2,4-a-methanonaphthalene-1(5H)-one | woody aroma with green, tart, cardamom-like undertones. |
| F. Hexahydro-1,2,5,5-tetramethyl-2H-2,4-a-methanonaphthalene-1(5H)-one | sweet, woody, camphoraceous, balsamic aroma with patchouli and deep woody undertones. |

EXAMPLE XVI

PREPARATION OF LIQUID DETERGENT

Concentrated liquid detergents with aromas as set forth below containing 0.2%, 0.5% and 1.2% of the compositions as set forth in the table below are prepared by adding the appropriate quantity of the indicated composition as set forth below to liquid detergent known as P-87. The aromas of the liquid detergent increase with increasing concentration of composition as set forth in the table below:

TABLE II

| DESCRIPTION OF COMPOSITION | FRAGRANCE CHARACTERISTICS |
|---|---|
| A. Fragrance of Example X | amber, woody and earthy |
| B. Fragrance of Example XI | vetiver with intense varnishy, woody note and excellent green, tart, cardamom-like nuances |
| C. Hexahydro-5,5-dimethyl-2H-2,4-a-methanonaphthalene-2(5H)-one | sweet, woody, camphoraceous aroma with minty and ambery nuances |
| D. Hexahydro-2,5,5-trimethyl-2H-2,4-a-methanonaphthalene-1(5H)-one | a low-keyed, oily, woody, amber aroma with woody and slightly leathery undertones. On purification a deep woody, earthy camphoraceous, patchouli-like aroma with amber and leathery undertones. |
| E. Hexahydro-1,5,5-trimethyl-2H-2,4-a-methanonaphthalene-1(5H)-one | woody aroma with green, tart, cardamom-like undertones. |
| F. Hexahydro-1,2,5,5-tetramethyl-2H-2,4-a-methanonaphthalene-1(5H)-one | sweet, woody, camphoraceous, balsamic aroma with patchouli and deep woody undertones. |

EXAMPLE XVII

A tobacco blend is prepared as follows:

| Ingredient | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

The following flavor formulation is prepared:

| Ingredient | Parts by Weight |
|---|---|
| Ethyl Butyrate | 0.05 |
| Ethyl Valerate | 0.05 |
| Maltol | 2.00 |
| Cocoa Extract | 26.00 |
| Coffee Extract | 10.00 |
| 95% Ethanol (aqueous) | 20.00 |
| Water | 41.90 |

The above-mentioned tobacco blend is divided into four portions: Portion A; Portion B; Portion C; and Portion D. Portion C and D are each combined separately with the above-mentioned tobacco flavor formulation, at the rate of 0.2%. Each of Portions A, B, C and D are then manufactured into cigarettes. The cigarettes containing tobacco Portions A and C are left as is. To the cigarettes manufactured from tobacco Portions B and D is added at the rates of 200 and 2000 ppm hexahydro-2,5,5-trimethyl-2H-2,4-a-methanonaphthalene-1(5H)-one prepared according to Example VIII. The cigarettes are then evaluated by paired comparison and the results are as follows.

The aroma on smoking of cigarettes produced from tobacco Portions B and D is found to be more sweet, floral, woody, spicy and leathery-like with enhanced tobacco taste and tobacco aroma, than the aroma of those cigarettes produced from Portions A and C.

In smoke flavor (main stream) the cigarettes produced from Portion D are found to be more aromatic and sweeter with a cooling effect.

In smoke flavor (side stream or room aroma) the cigarettes produced from Portion D are found to be sweet, aromatic, more woody and more spicy, e.g., having an oriental, balsamic character.

Thus, the product produced according to Example VIII modifies the side stream and the main stream smoke aromas at making it more pleasant and more natural tobacco-like.

All cigarettes are evaluated for smoke flavor with a 20 mm cellulose acetate filter.

EXAMPLE XVIII

Utilizing the procedure of Example I of Column 15 of U.S. Pat. No. 3,632,396, a nonwoven cloth substrate useful as a dryer-added fabric softening article of manufacture is prepared wherein the substrate, the substrate coating and the outer coating and the perfuming material are as follows:

1. a water "dissolvable" paper ("Dissolvo Paper"):
2. Adogen 448 (m.p. about 140° F.) as the substrate coating; and
3. an outer coating having the following formulation (m.p. about 150° F.):
   57 percent $C_{20-22}$HAPS
   22 percent isopropyl alcohol
   20 percent antistatic agent
   1 percent of a composition as set forth in the table below having the aroma properties as set forth in the table below:

TABLE II

| DESCRIPTION OF COMPOSITION | FRAGRANCE CHARACTERISTICS |
|---|---|
| A. Fragrance of Example X | amber, woody and earthy |
| B. Fragrance of Example XI | vetiver with intense varnishy, woody note and excellent green, tart, cardamom-like nuances |
| C. Hexahydro-5,5-dimethyl-2H-2,4-a-methanonaphthalene-2(5H)-one | sweet, woody, camphoraceous aroma with minty and ambery nuances |
| D. Hexahydro-2,5,5-trimethyl-2H-2,4-a-methanonaphthalene-1(5H)-one | a low-keyed, oily, woody, amber aroma with woody and slightly leathery undertones. On purification a deep woody, earthy camphoraceous, patchouli-like aroma with amber and leathery undertones. |
| E. Hexahydro-1,5,5-trimethyl-2H-2,4-a-methanonaphthalene-1(5H)-one | woody aroma with green, tart, cardamom-like undertones. |
| F. Hexahydro-1,2,5,5-tetramethyl-2H-2,4-a-methanonaphthalene-1(5H)-one | sweet, woody, camphoraceous, balsamic aroma with patchouli and deep woody undertones. |

Fabric-softening compositions prepared as set forth below having the above aroma characteristics essentially consist of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of the substrate. The aromas as set forth in Table II above are imparted in a pleasant manner to the head space in the dryer on operation thereof using the said dryer added fabric softening nonwoven fabric.

EXAMPLE XIX

Granular detergent compositions prepared according to United Kingdom Patent Specification No. 1,501,498 having the following formulae are prepared by spray-drying the following mixtures as indicated in the columns headed XIX A, XIX B, XIX C and XIX D:

| Ingredient | COMPOSITION IN % BY WEIGHT | | | |
|---|---|---|---|---|
| | Example XIX A | Example XIX B | Example XIX C | Example XIX D |
| Sodium salt of ethoxylated fatty alcohol sulfate having an average of about 2.25 moles of ethylene oxide per mole of fatty alcohol (1) | 14.1 | 14.1 | 14.1 | 14.1 |
| Sodium tallow alkyl sulfate | 2.4 | 2.4 | 2.4 | 2.4 |
| Sodium silicate solids ratio: $SiO_2/Na_2O = 2.0$ | 0.0 | 2.0 | 6.0 | 0.0 |
| Sodium silicate solids ratio: $SiO_2/Na_2O = 3.2$ | 1.0 | 0.0 | 0.0 | 6.0 |
| Sodium tripolyphosphate | 24.0 | 24.0 | 24.0 | 24.0 |
| $Na_{12}(AlO_2 . SiO_2)_{12} 27H_2O$ (2) | 18.0 | 18.0 | 18.0 | 18.0 |
| Moisture | 10.0 | 10.1 | 9.9 | 10.2 |
| Sodium sulfate | 25.0 | 25.0 | 20.0 | 20.0 |
| Minor ingredients including sodium toluene sulfonate, trisodium sulfosuccinate, dyes, brighteners | 4.0 | 2.4 | 3.6 | 2.3 |
| hexahydro 15,5-dimethyl-2H-2,4-a-methanonaphthalene-1(5H)-one | 1.5 | 0.0 | 0.0 | 0.0 |
| hexahydro-2,5,5-trimethyl-2H-2,4-a-methanonaphthalene-1(5H)-one | 0.0 | 2.0 | 0.0 | 0.0 |
| hexahydro-1,5,5-trimethyl-2H-2,4-a-methanonaphthalene-1(5H)-one | 0.0 | 0.0 | 2.0 | 0.0 |
| hexahydro-1,2,5,5-tetramethyl-2H-2,4-a-methanonaphthalene-1(5H)-one | 0.0 | 0.0 | 0.0 | 3.0 |

(1) Fatty alcohol composition: 66% $C_{14}$; 33% $C_{16}$; 1% $C_{18}$.
(2) Prepared as described in United Kingdom Patent 1,501,498; average particle size diameter 2 microns.

Laundry solutions containing the above detergent compositions are used to launder fabrics. Each of the laundry compositions both prior to and on laundering gives rise to the following aromas:

| NAME OF COMPOUND | FRAGRANCE |
|---|---|
| hexahydro-5,5-dimethyl-2H-2,4-a-methanonaphthalene-1(5H)-one | sweet, woody, camphoraceous aroma with minty and ambery nuances |
| hexahydro-2,5,5-trimethyl-2H-2,4-a-methanonaphthalene 1(5H)-one | low-keyed, oily, woody, amber aroma with woody and slightly leathery undertones. On purification a deep woody, earthy camphoraceous, patchouli-like aroma with amber and leathery undertones |
| hexahydro-1,5,5-trimethyl-2H-2,4-a-methanonaphthalene-1(5H)-one | woody aroma with green, tart, cardamom-like undertones |
| hexahydro-1,2,5,5-tetramethyl-2H-2,4-a-methanonaphthalene-1(5H)-one | sweet, woody, camphoraceous, balsamic aroma with patchouli and deep woody undertones |

EXAMPLE XX

PERFUMED LIQUID DETERGENT

Concentrated liquid detergents having aromas as set forth on the table below are prepared containing 0.10%, 0.15%, 0.20%, 0.40% and 0.80% of one of the materials as set forth in the table below. They are prepared by adding and homogeneously mixing the appropriate quantity of mixture of perfume materials in liquid detergent. The liquid detergent is a builder-free liquid detergent consisting of (a) 50% of a non-ionic surfactant having an HLB of 8.0 and a critical micelle concentration of 0.007, weight percent at 25° C.; (b) an ionic surfactant which is triethanolamine citrate; and (c) one weight percent of diethanolamine prepared according to United Kingdom Patent Specification No. 1,491,603.

The detergents all possess fragrances as set forth in the table below, the intensity increasing with greater concentrations of fragrance material:

TABLE II

| DESCRIPTION OF COMPOSITION | FRAGRANCE CHARACTERISTICS |
|---|---|
| A. Fragrance of Example X | amber, woody and earthy |
| B. Fragrance of Example XI | vetiver with intense varnishy, woody note and excellent green, tart, cardamom-like nuances |
| C. Hexahydro-5,5-dimethyl-2H-2,4-a-methanonaphthalene-2(5H)-one | sweet, woody, camphoraceous aroma with minty and ambery nuances |
| D. Hexahydro-2,5,5-trimethyl-2H-2,4-a-methanonaphthalene-1(5H)-one | a low-keyed, oily, woody, amber aroma with woody and slightly leathery undertones. On purification a deep woody, earthy camphoraceous, patchouli-like aroma with amber and leathery undertones. |
| E. Hexahydro-1,5,5-trimethyl-2H-2,4-a-methanonaphthalene-1(5H)-one | woody aroma with green, tart, cardamom-like undertones. |
| F. Hexahydro-1,2,5,5-tetramethyl-2H-2,4-a-methanonaphthalene-1(5H)-one | sweet, woody, camphoraceous, balsamic aroma with patchouli and deep woody undertones. |

What is claimed is:

1. A process for augmenting or enhancing the aroma or taste of a smoking tobacco comprising the step of adding to a smoking tobacco an aroma or taste augmenting or enhancing quantity of at least one tricyclic ketone having the structure:

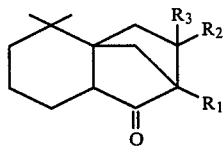

wherein $R_1$, $R_2$ and $R_3$ are the same or different and each represents hydrogen or $C_1$–$C_3$ lower alkyl.

2. A smoking tobacco composition comprising smoking tobacco and intimately admixed therewith in an aroma or taste augmenting or enhancing quantity, at least one tricyclic ketone having the structure:

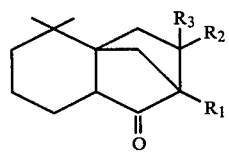

wherein $R_1$, $R_2$ and $R_3$ are the same or different and each represents hydrogen or $C_1$–$C_3$ lower alkyl.

3. A smoking tobacco article comprising a cylindrically shaped body of smoking tobacco, along the length of said cylindrically shaped body, a wrapper, and at one end of the cylindrically shaped body, a filter, and intimately admixed in an aroma augmenting or enhancing quantity with said filter, said wrapper or said cylindrically shaped body of smoking tobacco, at least one tricyclic ketone having the structure:

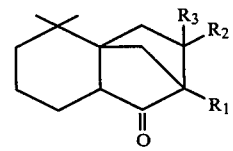

* * * * *

UNITED STATES PATENT AND TRADEMARK OFFICE
CERTIFICATE OF CORRECTION

PATENT NO. : 4,285,349

DATED : August 25, 1981

INVENTOR(S) : Mark A. Sprecker, James M. Sanders, William L. Schreiber, Hugh Watkins, Joaquin F. Vinals, Edward J. Shuster, Thomas J. O'Rourke, Myrna L. Hagedorn, Philip Klemarczyk It is certified that error appears in the above-identified patent and that said Letters Patent are hereby corrected as shown below:

Column 36, line 46 add:

---wherein $R_1$, $R_2$ and $R_3$ are the same or different and each represents hydrogen or $C_1$-$C_3$ lower alkyl.---

Signed and Sealed this

Eleventh Day of February 1986

[SEAL]

Attest:

DONALD J. QUIGG

Attesting Officer

Commissioner of Patents and Trademarks